(12) United States Patent
Ovenden et al.

(10) Patent No.: US 8,620,709 B2
(45) Date of Patent: Dec. 31, 2013

(54) MOBILE ACTIVITY MANAGER

(75) Inventors: Francis A. Ovenden, Groton, MA (US);
Silvana D. Romagnino, Ottawa (CA);
Jodee Varney, Lincoln, MA (US);
Bradley R. Black, Carp (CA); Thomas P. Chmara, Richmond (CA)

(73) Assignee: Avaya, Inc, Basking Ridge, NJ (US)

( * ) Notice: Subject to any disclaimer, the term of this patent is extended or adjusted under 35 U.S.C. 154(b) by 0 days.

(21) Appl. No.: 13/372,437

(22) Filed: Feb. 13, 2012

(65) Prior Publication Data
US 2012/0209649 A1    Aug. 16, 2012

Related U.S. Application Data

(60) Provisional application No. 61/441,781, filed on Feb. 11, 2011.

(51) Int. Cl.
*G06Q 10/00*    (2012.01)
(52) U.S. Cl.
USPC ....... 705/7.15; 705/7.11; 705/7.12; 705/7.13; 705/7.14
(58) Field of Classification Search
USPC .................. 705/7.11–7.42; 709/205; 715/701
See application file for complete search history.

(56) References Cited

U.S. PATENT DOCUMENTS

| | | | |
|---|---|---|---|
| 6,551,243 B2 * | 4/2003 | Bocionek et al. | 600/300 |
| 6,750,766 B1 * | 6/2004 | Heitner et al. | 340/525 |
| 6,917,962 B1 * | 7/2005 | Cannata et al. | 709/204 |
| 7,640,548 B1 * | 12/2009 | Yu et al. | 718/106 |
| 8,041,583 B2 * | 10/2011 | Albro et al. | 705/3 |
| 8,292,807 B2 * | 10/2012 | Perkins et al. | 600/301 |
| 2002/0052771 A1 * | 5/2002 | Bacon et al. | 705/8 |
| 2003/0050800 A1 * | 3/2003 | Brandt et al. | 705/2 |
| 2003/0125987 A1 * | 7/2003 | Rucker | 705/3 |
| 2003/0135659 A1 * | 7/2003 | Bellotti et al. | 709/313 |
| 2004/0088678 A1 * | 5/2004 | Litoiu et al. | 717/104 |
| 2005/0010640 A1 * | 1/2005 | Cannata et al. | 709/205 |
| 2005/0021629 A1 * | 1/2005 | Cannata et al. | 709/205 |
| 2005/0021630 A1 * | 1/2005 | Cannata et al. | 709/205 |
| 2005/0193063 A1 * | 9/2005 | Cannata et al. | 709/205 |
| 2006/0212286 A1 * | 9/2006 | Pearson et al. | 704/9 |
| 2007/0005413 A1 | 1/2007 | Hennings | |
| 2007/0168861 A1 * | 7/2007 | Bell et al. | 715/701 |
| 2008/0168453 A1 | 7/2008 | Hutson, II | |
| 2008/0208615 A1 | 8/2008 | Banavar et al. | |
| 2009/0013047 A1 * | 1/2009 | Adreon et al. | 709/206 |

(Continued)

OTHER PUBLICATIONS

Merz, Michael, Boris Liberman, and W. Lam Ersdorf. "Using mobile agents to support interorganizational workflow management." Applied Artificial Intelligence 11.6 (1997): 551-572.*

(Continued)

*Primary Examiner* — Alan S Miller

(57) ABSTRACT

A computer-implemented method for handling a microflow includes receiving a workflow request that includes a task associated with the workflow and a contact address associated with the task, performing an operation associated with receiving the workflow request that includes at least one of opening a communication session with the contact address and sending a response to the workflow request to the contact address. The method further includes storing the task, prioritizing the task, and performing an operation associated with execution of the workflow including at least one of opening a communications session with the contact address, sending a status associated with performance of the task, and sending a completion status of the task.

20 Claims, 30 Drawing Sheets

(56) References Cited

U.S. PATENT DOCUMENTS

2009/0164253 A1* 6/2009 Lyshkow .................... 705/3
2009/0264102 A1* 10/2009 Parmar et al. ................ 455/411
2012/0303384 A1* 11/2012 Stepaniak et al. ............ 705/2

OTHER PUBLICATIONS

Hoo Sang Ko, Shimon Y. Nof, Design and application of task administration protocols for collaborative production and service systems, International Journal of Production Economics, vol. 135, Issue 1, Jan. 2012, pp. 177-189, ISSN 0925-5273, http://dx.doi.org/10.1016/j.ijpe.2011.06.005.*

Merz, Michael, et al. "Interorganizational workflow management with mobile agents in cosm." (1996).*

Meng, Jie, Sumi Helal, and Stanley Su. "An ad-hoc workflow system architecture based on mobile agents and rule-based processing." Proceedings of the 2000 international conference on artificial intelligence (ICAI2000), Las Vegas. 2000.*

Abecker, Andreas, et al. "Information supply for business processes: coupling workflow with document analysis and information retrieval." Knowledge-based systems 13.5 (2000): 271-284.*

* cited by examiner

MOBILE ACTIVITY MANAGER

REFERENCE TO RELATED APPLICATIONS

This application claims priority to U.S. Provisional Patent Application No. 61/441,781, filed Feb. 11, 2011, which is incorporated by reference.

TECHNICAL FIELD

The systems and methods described below relate generally to the field of task management systems that include communication functionality. More particularly, the systems and methods relate to facilitating collaboration between parties by integrating communication aspects into a task workflow system.

SUMMARY

Figure 1:
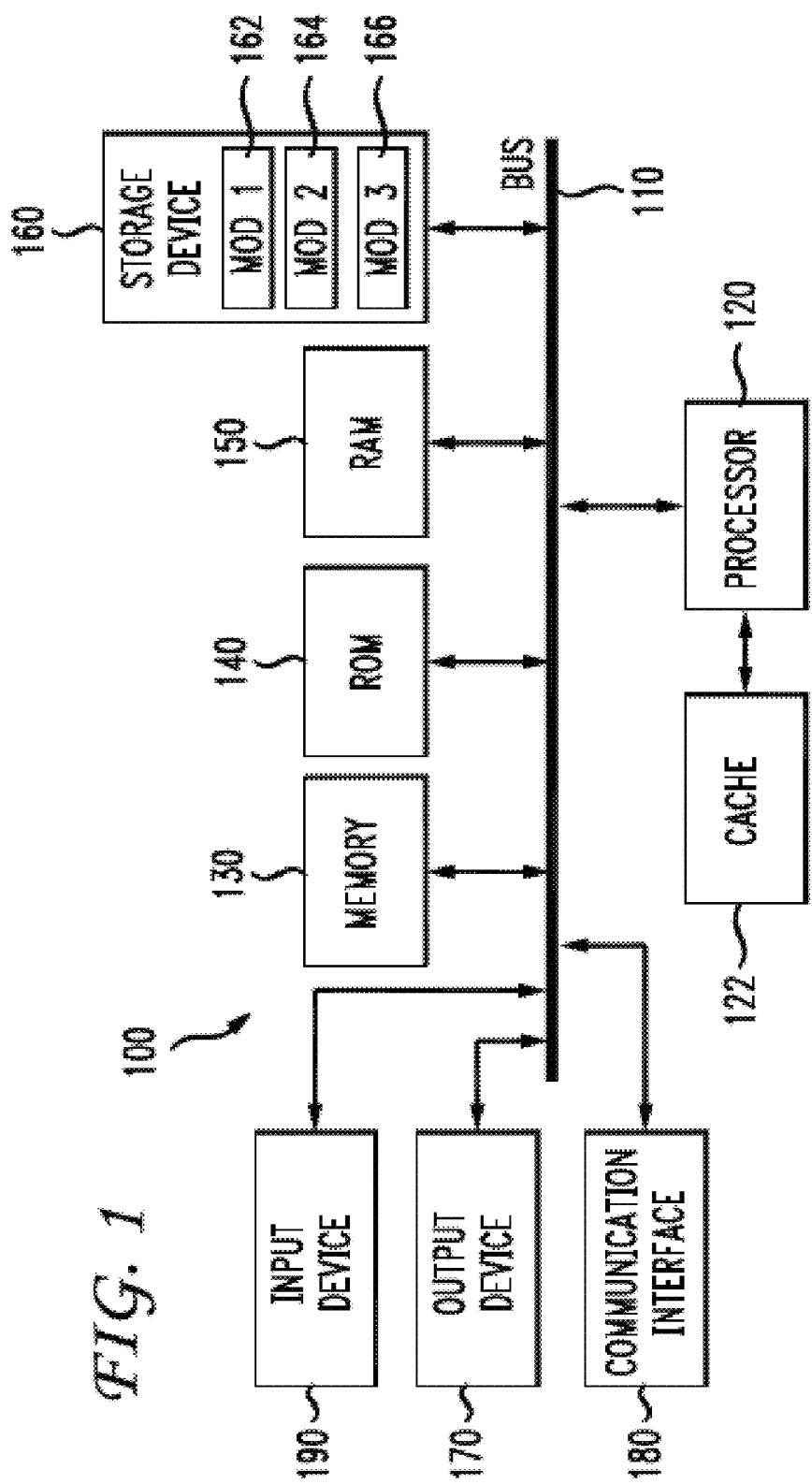
FIG. 1 is a block diagram of a computing device.

The systems and methods described here combine workflow and task management features with collaborative communication capabilities to provide an integrated task management system. The task management system consolidates tasks, messages, alerts, and notifications for workers and facilitates communications between parties. The task management system can use contextually available information relating to the tasks, messages, alerts, notifications, and communications to optimize efficiency, and ensure that tasks and messages are prioritized and timely completed.

A computer-implemented method for handling a microflow comprises receiving a workflow request at a processor that includes a task associated with the microflow and a contact address associated the task; performing an operation associated with receiving the workflow request that includes at least one of opening a communication session with the contact address at the processor, and sending a response to the workflow request addressed to the contact address from the processor; storing the task in a workflow queue in a memory; prioritizing the task at the processor; and performing an operation at the processor that is associated with execution of the microflow and that includes at least one of opening a communication session with the contact address, sending a status associated with performance of the task, and sending a completion status of the task.

The computer-implemented method can use a response selected from at least one of an acceptance of the workflow request, an inquiry regarding the workflow request, a rejection of the workflow request, and a request to defer an acceptance of the workflow request. The communication session, the response, the status, and the completion status can be transmitted in accordance with a medium selected from the group consisting of a text message, a multimedia message, an email message, a voice call, a video call, a conference call, a web-based session using a uniform resource locator, and a call to an interactive voice response system.

The computer-implemented method can include an operation associated with execution of the microflow for presenting the task at a human machine interface, and can include displaying an icon associated with the type of task, displaying a shape associated with a priority of the task, displaying a color coding associated with the priority of the task, displaying a shading associated with the priority of the task, displaying an alert, presenting an audible message about the task, presenting an audible alert, and presenting a vibratory alert. The computing-implemented method can further include an operation associated with execution of the microflow for receiving a selection of the task at a human machine interface, and sending at least one of a call request and a message to the contact address associated with the task from the processor.

In the computer-implemented method, the workflow request can also include at least one of a requested priority, a requested start time, a requested completion time, a requested length of time to complete the task, and a location for performance of the task. Also, the task can be prioritized based at least in part on at least one of the requested start time, the requested completion time, the requested length of time to complete the task, and a priority based at least in part on at least one of the requested priority, a priority set by a user override, and a priority set in accordance to at least one of a business policy rule associated with the task, and a regulatory compliance rule associated with the task.

The computer-implemented method can further comprise presenting the workflow request at a human machine interface; and receiving an input for responding to the workflow request at the human machine interface. The response to the workflow request is based at least in part upon the input. The computer-implemented method can further comprise receiving a message that includes at least one of a rescind notification of the workflow request, a reprioritization of the task, and a notification to remove the task from the workflow queue.

A computer-readable storage medium has computer-executable instructions stored thereon to instruct a processor to perform a method that comprises sending, to a first recipient, a workflow request that is associated with a microflow, and that includes a task and a contact address for addressing a message related to the task; receiving a response to the workflow request; receiving a status associated with performance of the task; and logging, in a memory, at least one of the workflow request, a timestamp associated with sending the workflow request, the response to the workflow request, a timestamp associated with receiving the response, the status associated with performance of the task, and a timestamp associated with receiving the status.

The processor can further perform the operations of escalating the workflow request at the expiration of an escalation timer and prior to receiving a least one of a response to the workflow request and a status associated with performance of the task; and sending the workflow request to a second recipient. The second recipient is selected from the group consisting of an originator of the workflow request, an alternate recipient of the workflow request, a peer group associated with the first recipient, a peer group associated with the second recipient, and an administrator. The workflow request can include at least one parameter selected from the group consisting of an address of a first recipient, an identification of the type of task, an address associated with the contact address, a preferred medium associated with the contact address, a requested priority, a requested start time, a requested completion time, a requested length of time to complete the task, and a location for performance of the task. The processor can change the parameter in accordance to at least one of a business policy rule associated with the task, and a regulatory compliance rule associated with the task.

A system for handling a microflow comprises a computing device having a processor configured to receive a workflow request that is associated with the microflow that includes a task, and a contact address associated with the task, perform an operation associated with receiving the workflow request that includes at least one of opening a communication session with the contact address, and sending a response to the workflow request that is addressed to the contact address, store the task in a workflow queue, prioritize the task, and perform an operation associated with execution of the microflow that includes at least one of opening a communication session with the contact address, sending a status associated with performance of the task, and sending a completion status of the task. The system further comprises a memory configured to store a workflow queue; and a communications interface configured to handle at least one of the communication session, and a message. In a configuration, the computing device is a mobile computing device, and the communications interface is a wireless communications interface.

In the system, the response can be selected from at least one of an acceptance of the workflow request, an inquiry regarding the workflow request, a rejection of the workflow request, and a request to defer an acceptance of the workflow request. The system can further comprise a human-machine interface that can include a display configured to present at least one of the workflow request, the task, the contact address, a display of an icon associated with the type of task, a display of a shape associated with a priority of the task, a display of a color associated with the priority of the task, a display of a shading associated with the priority of the task, and a display of an alert; an audible element configured to present at least one of an audible message about the task, and an audible alert; a vibratory element configured to present a vibratory alert; and an input means for accepting an input.

The processor can be configured to present the workflow request using the human-machine interface and receive an input from the human-machine interface. The response to the workflow request can be based at least in part upon the input. The workflow request can include at least one of a requested priority, a requested start time, a requested completion time, a requested length of time to complete the task, and a location for performance of the task. The processor can be further configured to prioritize the task based at least in part on the requested start time, the requested completion time, the requested length of time to complete the task, and a priority based at least in part on at least one of the requested priority, a priority set by a user override, and priority set in accordance to at least one of a business policy rule associated with the task, and a regulatory compliance rule associated with the task. The message can be the response, the status, the completion status, and an inquiry associated with the task, and the medium for the message can be selected from the group consisting of a text message, a multimedia message, an email message, a voice call, a video call, a conference call, a web-based session using a uniform resource locator, and a call to an interactive voice response system.

DETAILED DESCRIPTION

The apparatuses, devices, systems and methods disclosed and described in this document can be used to handle task management aspects and communication aspects of an integrated task management system. Those of ordinary skill in this art area will recognize from reading this description that the apparatuses, devices, methods, and systems described can be applied to, or easily modified for use with, other types of equipment, other arrangements of computing systems such as client-server, peer-to-peer, or distributed systems, other protocols, and at other layers in communication protocol stacks.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware. The term software is used expansively to include not only executable code, but also data structures, data stores and computing instructions in any electronic format, firmware, and embedded software. The terms information and data are used expansively and includes a wide variety of electronic information, including but not limited to machine-executable or machine-interpretable instructions; content such as text, video data, and audio data, among others; and various codes or flags. The terms information, data, and content are sometimes used interchangeably when permitted by context. It should be noted that although for clarity and to aid in understanding some examples discussed below might describe specific features or functions as part of a specific component or module, or as occurring at a specific layer of a computing device (for example, a hardware layer, operating system layer, or application layer), those features or functions may be implemented as part of a different component or module or at a different layer.

The examples discussed below are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

FIG. 1 illustrates an exemplary computing device 100. The computing device 100 can a desktop computer, a server, a mobile computing device such as a smartphone, or any other suitable computing device as would be understood in the art. The computing device 100 includes a processor 120 that can be any suitable type of processing unit, for example a general purpose central processing unit (CPU), a reduced instruction set computer (RISC), a processor that has a pipeline or multiple processing capability including having multiple cores, a complex instruction set computer (CISC), a digital signal processor (DSP), an application specific integrated circuits (ASIC), a programmable logic devices (PLD), and a field programmable gate array (FPGA), among others.

The computing device 100 also includes one or more memories 130, for example read only memory (ROM) 140, random access memory (RAM) 150, cache memory 122 associated with the processor 120, or other memories such as dynamic RAM (DRAM), static ram (SRAM), flash memory, a removable memory card or disk, a solid state drive, and so forth. The computing device 100 also includes storage media such as a storage device 160 that can be configured to have multiple modules 162, 164, 166, such as magnetic disk drives, floppy drives, tape drives, hard drives, optical drives and media, magneto-optical drives and media, compact disk drives, Compact Disk Read Only Memory (CD-ROM), Compact Disk Recordable (CD-R), Compact Disk Rewriteable (CD-RW), a suitable type of Digital Versatile Disk (DVD) or BluRay disk, and so forth. Storage media such as flash drives, solid state hard drives, redundant array of individual disks (RAID), virtual drives, networked drives and other memory means including storage media on the processor 120 or memories 130 are also contemplated as storage device 160.

The memory 130, processor 120, and storage drive 160 can include nonvolatile memory for storing computer-readable instructions, data, data structures, program modules, code, microcode, and other software components for storing the computer-readable instructions in non-transitory computer-readable mediums in connection with the other hardware components for carrying out the methodologies described herein. Software components can include source code, compiled code, interpreted code, executable code, static code, dynamic code, encrypted code, or any other suitable type of code or computer instructions implemented using any suitable high-level, low-level, object-oriented, visual, compiled, or interpreted programming language.

In various configurations, the computing device 100 can include a system bus 110 for interconnecting the various components of the computing device 100, or the computing device 100 can be integrated into one or more chips such as programmable logic device or application specific integrated circuit (ASIC). The system bus 110 can include a memory controller, a local bus, or a peripheral bus for supporting input devices 190, output devices 170, or communication interfaces 180. Example input devices 190 and output devices 170 include keyboards, keypads, gesture or graphical input devices, motion input devices, touchscreen interfaces, displays, audio units, voice recognition units, vibratory devices, computer mice, and any other suitable user interface.

The communication interface 180 allows the computing device 100 to communicate with other device across a network. The communication interface 180 can be an Ethernet interface, a radio interface, a telephony interface, a Universal Serial Bus (USB) interface, or any other suitable communications interface. Example communication interfaces 180 can includes wired data transmission links such as Ethernet and TCP/IP, as well as PSTN communications links such as Tls (or better), integrated services digital network (ISDN), Digital Subscriber Line (DSL), or dialup modems that implement, for example, the point-to-point protocol (PPP). The communication interface 180 can include wireless protocols for interfacing with private or public networks. For example, the communication interface 180 and protocols can include interfaces for communicating with private wireless networks such as a WiFi network, one of the IEEE 802.11x family of networks, or another suitable wireless network. The communication interface 180 and protocols can include interfaces for communicating with public wireless networks, such as cellular networks.

Figure 2:
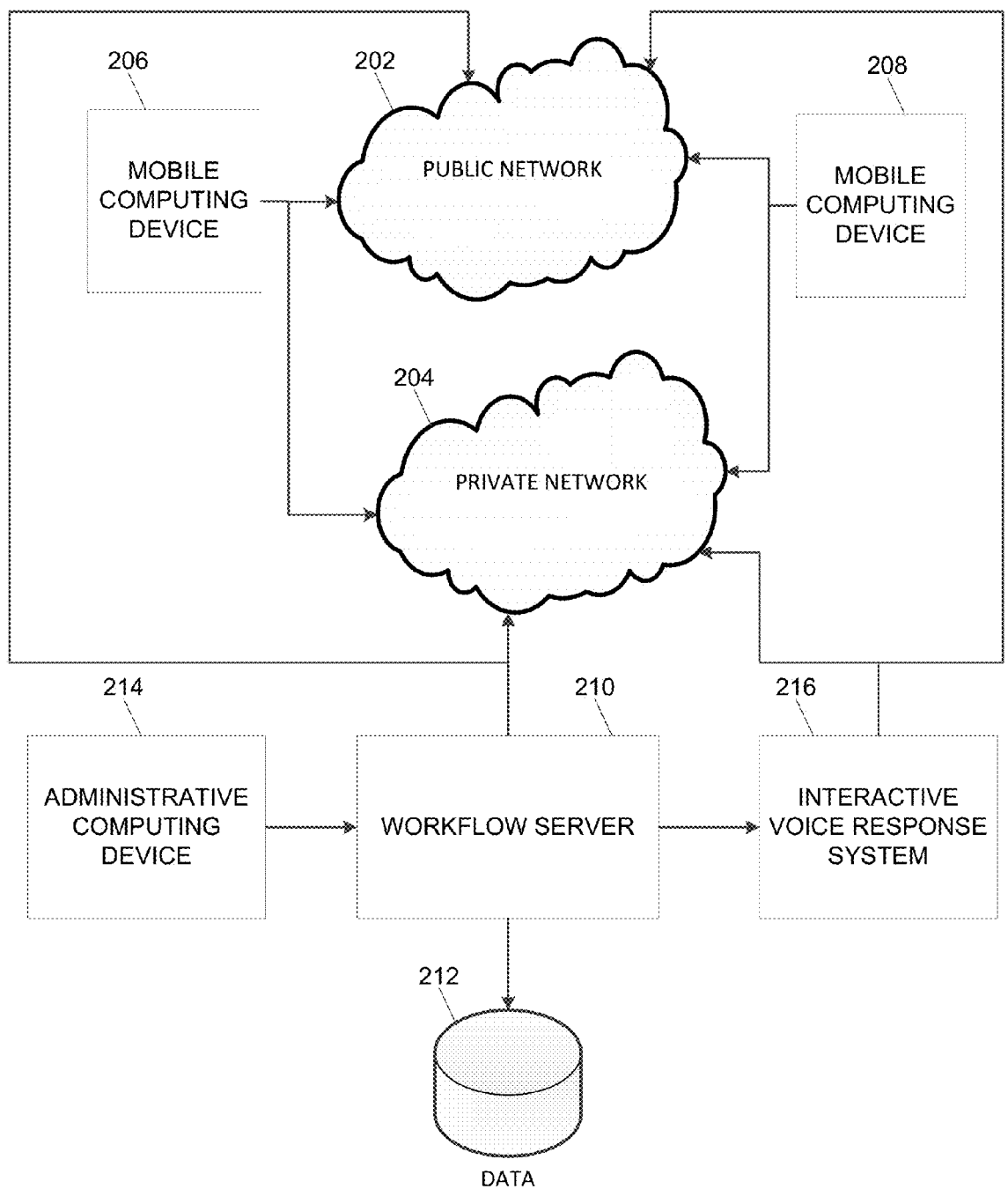
FIG. 2 is a block diagram of a task management system.

FIG. 2 illustrates a block diagram of networked computing devices configured as a task management system 200. Although illustrated as including both a public network 202 and a private network 204, this is done for purposes of illustration only. In various configurations the task management system 200 can be implemented using only one network 202, 204, a combination of a public network 202 and a private network 204, and any other suitable combination including multiple public networks 202 and multiple private networks 204. Each network 202, 204 can be, for example, an intranet, the Internet, a telephone network, a cable network, a wireless network, a packet-switched network, a circuit-switched network, or any other suitable network. Example networks can include an asynchronous transfer mode (ATM) network, a packet-switched network running, for example, the TCP/IP suite of protocols, a wireless network running one or more of the IEEE 802.11x, IEEE 802.15, or IEEE 802.16 family of protocols (WiFi and Zigbee, among others), a cellular network using code division multiple access (CDMA or CDMA: 2000), global system for mobile communications (GSM), a cellular network running a 3G or 4G protocol, or another suitable network, including networks using protocols currently in development or yet to be developed.

The task management system 200 can be configured to use secure communication protocols such as Internet Protocol security (IPsec), Secure Sockets Layer (SSL), Transport Layer Security (TLS), secure hypertext transfer protocol (HTTPS/1.1) or any other suitable encrypted protocol. Encryption can also be performed using a suitable type of cipher, including a private key cipher, a symmetric private key cipher, a public key cipher, and an elliptic curve cipher, among others. Specifically, encryption can be implemented using the Advanced Encryption Standard (AES), the Data Encryption Standard (DES), triple DES (3DES), or another suitable cipher.

The task management system 200 can include a first mobile computing device 206, a second mobile computing device 208, an administrative computing device 214, a workflow server 210, a data store 212, and an interactive voice response system 216. As will be described in more detail herein, a user of the first mobile computing device 206 can send a workflow request 301 to the user of the second mobile computing device 208. Either of the users can open a communication session between the mobile computing devices 206, 208, for example to discuss a workflow request 301 or performance of tasks. Communication sessions can include those normally associated with telephony services or the communication sessions can be internet-based communications such as voice over internet protocol (VoIP). Either of the users can send messages to the mobile computing device 206, 208 of another user. Messages can include text messages, pictures or images, audio, or video, and can be short message service (SMS) messages, multimedia message service (MMS) messages, and other suitable message types. The mobile computing devices 206, 208 can also receive notifications, and alerts that can be readable text or data such as a structured set of data.

The messages can be acknowledged messages and include a response set, for example a read receipt, an acknowledgement (ACK), an indication of not acknowledged (NACK), and a call back indication among other message types. A response set can be contextually-relevant to the task or tasks in a workflow request, and can include a predetermined response sequence order. The messages can be selected from a list, can be part of an interactive text session, can include forms, can include uniform resource locators (URL), and can launch applications and plug-ins, and so forth. The response set may include the selection of one or more of a set of offered choices that answer an associated prompt.

The workflow requests, messages, communication requests, notifications, and alerts can be sent from other mobile computing devices 206, 208, or from other client interfaces using desktop applications, web-based applications, and telephony clients among other suitable clients and interfaces. An application programming interface (API) can provide an interface for either clients or servers to communicate with mobile computing devices 206, 208 or the workflow server 210. The API can also allow other users or other systems to provide information to or create workflows on the task management system 200. Both users and servers can create workflows on the task management system 200.

A user of an administrative computing device 214 can configure workflow requests on the workflow server 210 that are sent to users of the mobile computing devices 206, 208. The user of the administrative computing device 214 can also perform supervisory functions such as monitoring the issuance of workflow requests to the mobile computing devices 206, 208 of the users, reviewing the performance and completion of tasks by the users, and performing analysis and determining metrics relating to task performance by the users.

The workflow server 210 can operate as a message and communications gateway between the mobile computing devices 206, 208. For example, the mobile computing devices 206, 208 and workflow server 210 can be configured as a client-server type architecture. In various configurations, the workflow server 210 can communicate workflow requests and receive acknowledgements and status updates from the users over one or more of the networks 202, 204. The workflow server 210 can also be integrated with an interactive voice response system (IVR) 216 for communicating with users using voice recognition or touchtone keypad interactions. The workflow server 210 can use one or multiple servers. The workflow server 210 can use one or multiple software modules and be split between multiple servers or aggregated onto a single server or virtual server.

The workflow server 210 can store workflow requests, messages, communications, alerts, and notifications, and logs of information relating to the workflow requests, messages, communications, alerts, and notification in the data store 212. The workflow server 210 can store time stamps for each of these events to facilitate later review and analysis. The logging and capturing of this information down to the individual message, permits both the users and the system administrator to review tasks and communications at a fine level of granularity. The workflow server 210 captures all of the related tasks, workflow requests, acknowledgements, notifications, alerts, messages, and communications that together make up a microflow, and permits the users and the administrator to review the sequence of individual events, user actions, and user interactions of the microflow. The users and administrator can review the microflow after completion of the tasks associated with the microflow, or during the execution of the microflow. A user may have visibility only into the portion of the workflow in which the user is participating, while the administrator typically has visibility of the entire workflow.

A workflow can describe a process for a major activity such as producing a video, or treating a patient in hospital. The workflow steps employed by different individuals may vary in the details but can also be quite similar. For example, best practices or regulatory guidelines can create similarities in workflow steps. Complex workflows are composed of smaller workflows and for team-working workflows may be decomposed into specialist activities or to share the workload to gain time efficiency through parallelism. The breakdown of a complex workflow continues until a unit of work is the right size and type to be a microflow. A microflow is one or more tasks including the workflow request associated with the one or more tasks, and any other related notifications, alerts, messaging, and communication sessions associated with the tasks or workflow requests.

Tasks can be assigned, revoked, reassigned, and completed by one or multiple users. Tasks in a workflow request 301 can generate multiple new tasks, each of which may be performed by the same user or different users working in collaboration. Completion of a task can depend on the completion status of other tasks being performed by other users. A workflow can also comprise a single task, sent in a workflow request 301 to a single user to be performed. The workflow server 210 captures logs and information regarding all of the related activities of workflows thereby permitting review, real-time and post analysis, and the development of performance metrics. Workflows can be analyzed to ensure that business policies are being adhered to and that regulatory policies are being complied with.

The workflow server 210 can be any kind of suitable server, including a virtual server operating over a network 202, 204, or multiple servers. The mobile computing device 206, 208 can be any kind of suitable computing device including, but not limited to a cell phone, a mobile phone, a smart phone, a computing tablet, a laptop, a portable computing device, and a computing device mounted in a moving platform, for example a vehicle, among other suitable platforms. Although the task management system 200 is illustrated with mobile computing devices 206, 208, in various configurations the task management system 200 can include non-mobile, or fixed, computing devices such as desktop computers, computing devices embedded in non-mobile platforms, and other non-mobile computing devices. Practical usage scenarios can have a mix of users using fixed computing devices and mobile computing devices.

Figure 3:
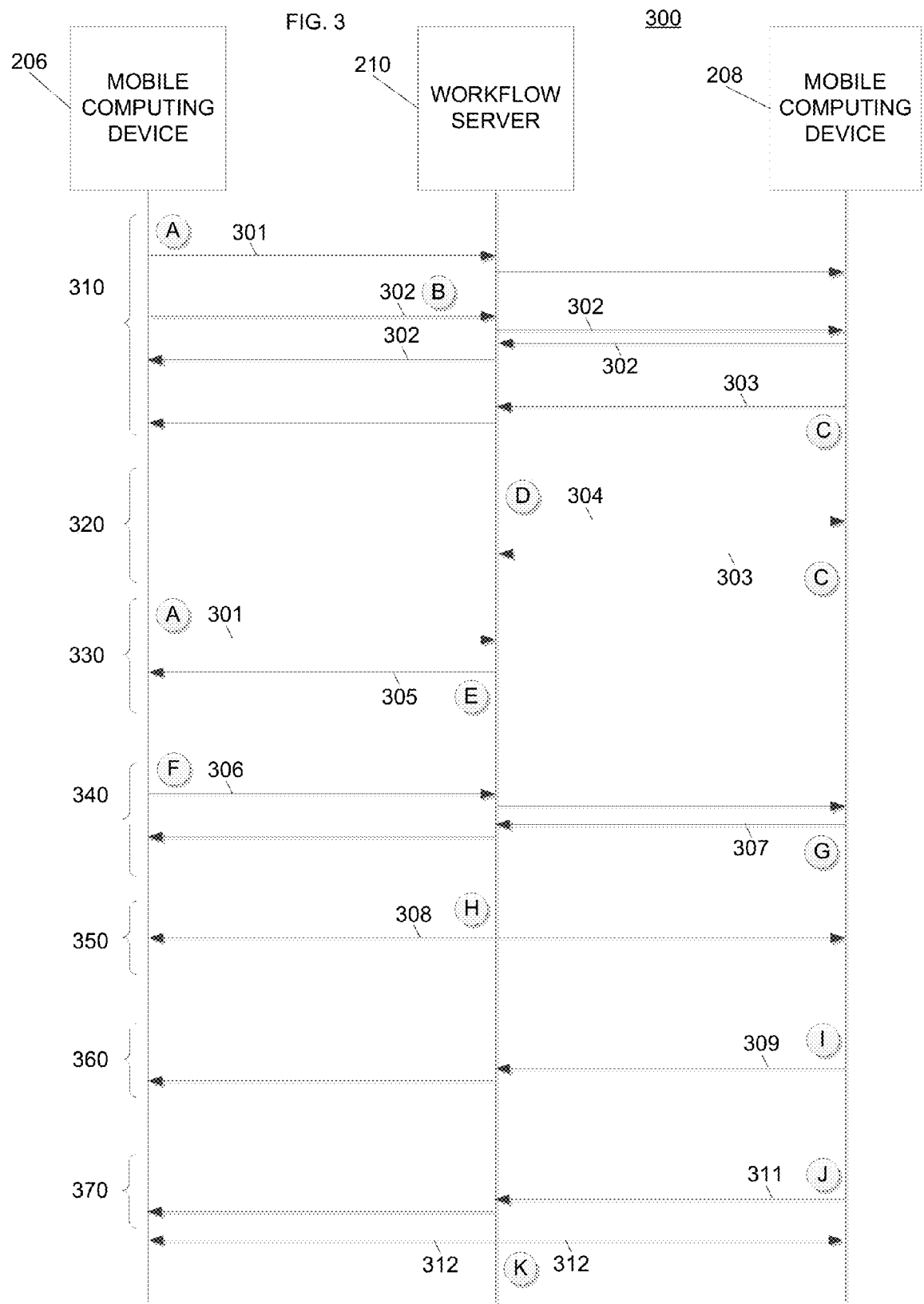
FIG. 3 is a timeline diagram of example operations of a task management system.

FIG. 3 illustrates an exemplary timeline of operations 300 performed by a task management system 200. The timeline of operations 300 visualized in FIG. 3 is for the purpose of illustrating some of the operations 310, 320, 330, 340, 350, 360, 370 possible in a task management system 200 and is not intended to illustrate the complete set of all possible operations 310, 320, 330, 340, 350, 360, 370. The operations 310, 320, 330, 340, 350, 360, 370 can be performed in a different order than presented, and are presented in the current order for purposes of providing a clear description only.

In a first operation 310, at point A in the timeline, a first user of a first mobile computing device 206 creates a workflow request 301 having a task to be performed, at least in part, by a second user of a second mobile computing device 208. The workflow request 301 passes through the workflow server 210 and is forwarded to the second mobile computing device 208. Once the workflow request 301 is received by the second user of the mobile computing device 208, the second user can select a response 303 at point C in the timeline and send that response 303 back to first user. The response 303 passes through the workflow server 210 and is forwarded to the first mobile computing device 206 of the first user. Although the first operation 310 is described for a workflow request 301 sent to a second user of a second mobile computing device 208, the second user and second mobile computing devices 310 can include multiple second users as well. For example, in a configuration the second user can be a group and the recipients of the workflow request 301 can include the mobile computing devices 208 of each member of the group. Similarly, this applies to the other operations 320, 330, 340, 350, 360, and 370.

Figure 4:
FIGS. 4-29 are plan views of a graphical user interface of a computing device.

Referring now to FIG. 3 and FIG. 4, an example of a workflow request 301 created at point A is illustrated. FIG. 4 illustrates a screenshot 400 for creating a new workflow request 301. The first user presses the new workflow selection 404 on the display 402 of the first mobile computing device 206. The first user is presented the option of creating a new workflow request 406, or selecting from a number of preconfigured workflow requests 408. The task management system 200 can use contextual information in determining which preconfigured workflow requests 408 to display to the first user. For example, the first user can see only the preconfigured workflow requests 408 that the first user has authority to send. The preconfigured workflow requests 408 can be ordered alphabetically, ordered based on frequency of use, or ordered based on other information such as time of day or recently sent or received workflow requests 301. The preconfigured workflow requests 408 can be grouped into folders of related workflows to facilitate selection, sorted by the first user, and searched by the first user. If permitted by the task management system, the first use can create a new workflow request 406.

The first user can also be a recipient of workflow requests 301. The first user can select the task selection 414 to review the current tasks assigned to the first user. The first user can select the sent selection 410 to review workflow requests 301 sent by the first user to recipients such as the second user. The first user can send workflow requests 301 to themselves as well, and therefore be both a recipient and a sender of the same workflow request 301. For example, the first user may want to send an alarm to their own mobile computing device 206 to remind them of an imminent event. The first user can also select the history selection 412 to review the history of sent and received actions of tasks that have ended. At this top level, the history selection 412 can be configured to show all tasks and actions of the first user. The first user can select one of the entries to display actions associated with the task, notification, alert or workflow request 301, as describe in the detailed description accompanying FIGS. 20 and 21.

Figure 5:
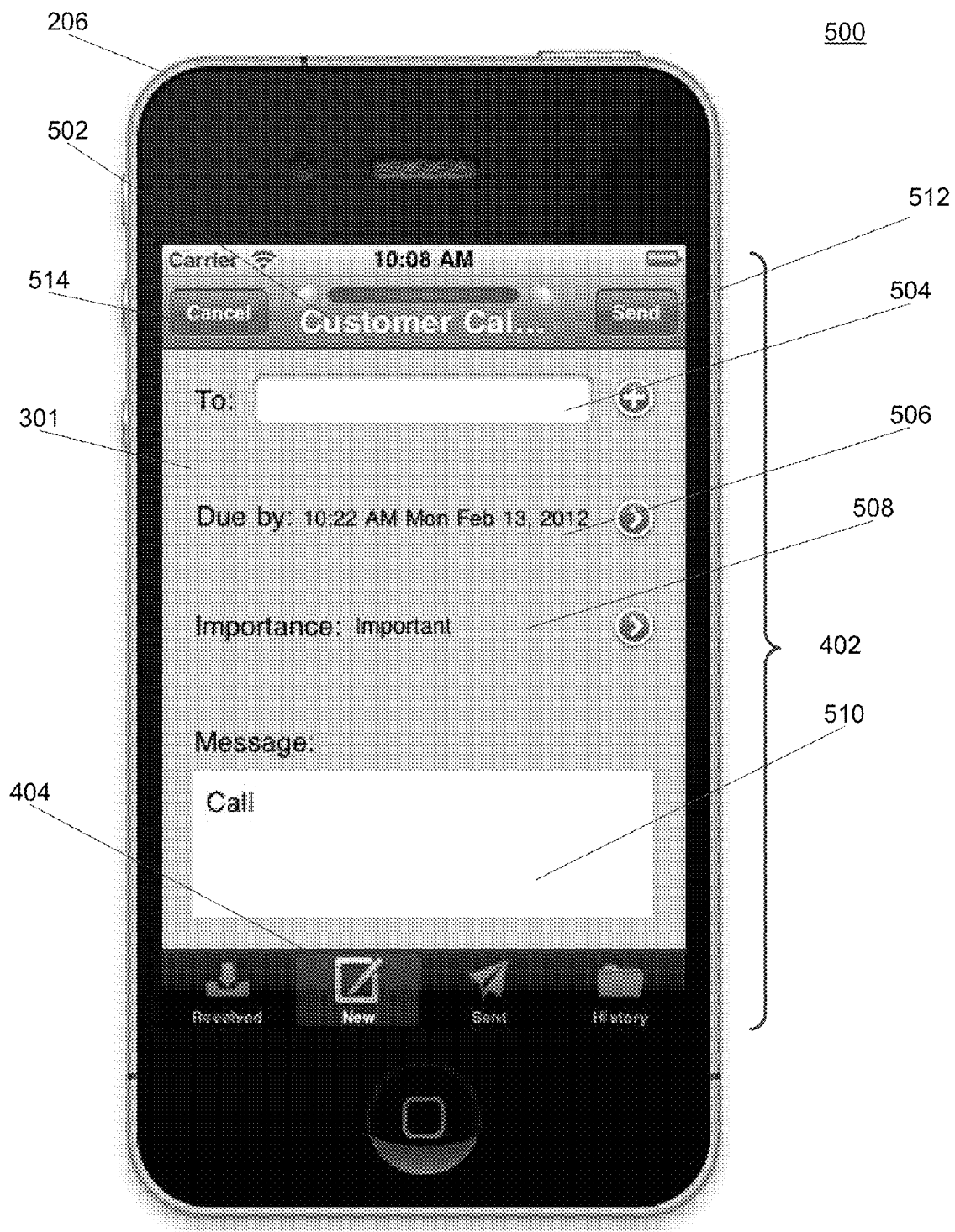

Referring now also to FIG. 5, a screenshot 500 illustrating an editable workflow request 301 is presented. The workflow request includes a workflow name 502. The first user can select or modify the contact address 504 of the recipient of the workflow request 301, the due time 506, the importance 508 of the workflow request 301, and optionally include a message 510 for the recipient of the workflow request 301. The first user can then press a send selection 512 to send the workflow request 301 or a cancel selection 514 if the first user opts not to send this workflow request 301.

The task associated with the workflow request 301 can be a process task, where the second user is requested to perform a task and respond appropriately with an acceptance and eventually a completion message once the task is performed. The task can be a notification or message, where a simple acknowledgement of the task completes the task. A task can also be a communications request, where one party requests the other party to open a communications session, after which the task is complete. The task can also be a voting task, where the workflow request 301 is sent to a group, and based on the responses 303, the first user picks one or more second users to perform the task. The task can also be a multiple choice question, where the second user is request to select a choice from one or more selections. For example, the multiple choice question can be, "When can you do this task", with possible selections "1—immediately", "2—in 1 hour", "3—today", "4—tomorrow", and "5—cannot perform".

The workflow request 301 also includes the contact address of the first user. This facilitates collaboration between the first user and second user, so that message can be easily sent and communication sessions can be easily initiated between the first user and the second user. For example, the acknowledgement options 1302 discussed later with regards to responses 303 from the second user to the workflow request 301 can include options for contacting the first user. For some tasks, such as tasks that are delegated, the workflow request can include one or more second contact address (not shown) to which the second user sends responses 303 and messages.

Figure 6:
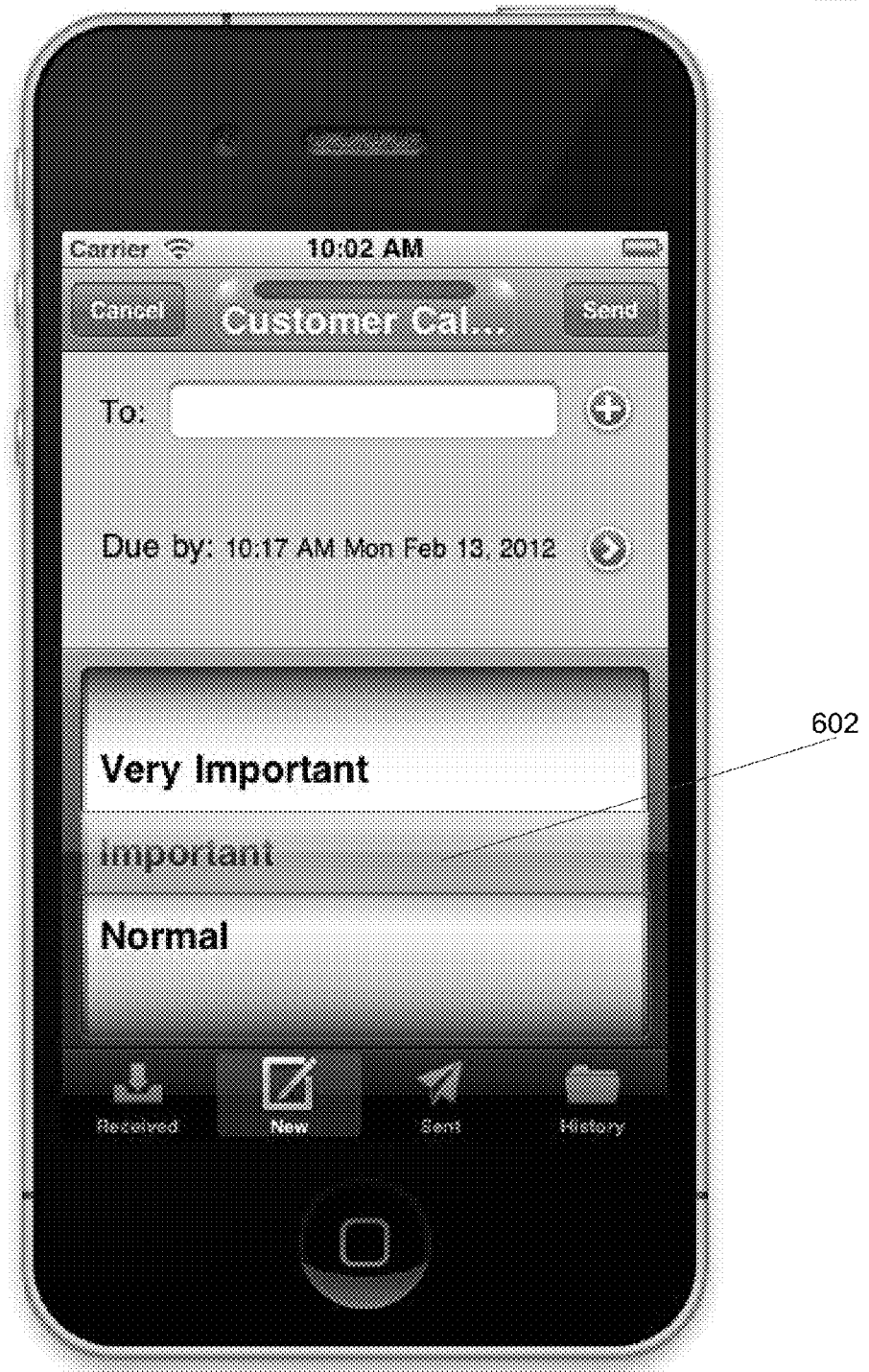

Referring now also to FIG. 6, a screenshot 600 illustrating an importance selection toolbar 602 is presented. In a configuration, if the first user attempts to modify the importance 508 of the workflow request 301, an importance selection toolbar 602 can be presented. The importance selection toolbar 602 facilitates in the selection of the appropriate importance 508 for the workflow request 301. Example importance 508 can include normal, important or very important. The importance 508 can be configured by the system administrator to suit the needs of their organization, and can have more or less than three levels. For example, a hospital may use the terms Normal, Stat, Emergency. The importance 508 can be configured to trigger an alert to the second user when the workflow request 301 is received by the second user. For example, a workflow request 301 configured to have an importance 508 of critical can cause a pop-up alert window, an audible alert, a vibratory alert, and so forth. The importance 508 can force the second user to acknowledge or otherwise respond to the workflow request 301. A screenshot 1400 of an alert 1402 is presented in FIG. 14 and the accompanying detailed description. In an alternate configuration, the importance 508 can include a measure of time urgency, for example critical, urgent, time sensitive, non-urgent, and so forth.

The importance selection toolbar 602 presents one way in which selectable options for importance 508 can be selected. As would be understood by those familiar in the art, this type of selection toolbar can be used for making selections for other fields displayed in other screenshots through this disclosure. The importance selection toolbar 602 is just one kind of toolbar possible; other kinds of toolbars and other types of graphical user interfaces known in the art, or yet to be developed, are also known or contemplated in this disclosure.

The importance 508 for a particular type of workflow request 301 can be preconfigured by a system administrator. The importance 508 can default to a particular importance 508 but a user can override the default importance 508 if desired. The importance 508 can also be limited to certain values. For example, a business policy or regulatory policy can prohibit setting the importance 508 to certain values, for example lowering the urgency below very important, or prevent the first user from modifying the importance 508 altogether. In another example, the ability to change the importance 508 can be limited to certain users, for example those users identified as supervisors or those users belonging to a supervisor group.

Similarly, the due time 506 can be a fixed selectable time, or a time interval added to the current time. For example, the first user can be presented with a choice of selecting a fixe time for the due time 506 or a time interval, for example 15 minutes, 30 minutes, an hour, a day, and so forth (not shown). If the first user selects the time interval, for example 15 minutes, then that time interval is added to the current time to produce the due time. The system administrator can preset a time interval for the task, which the first user can override.

The priority of a task can be derived from a combination, a product, or a weighting of other factors. The task management system 200 can use a strict priority algorithm, a weighted round robin algorithm, or another suitable algorithm based on business policies or regulatory policies. For example, priority can be a combination, a product, or a weighting of an importance factor and a time factor. The importance factor can be, for example, whether a task is of normal importance, high importance, or very important. The time factor can be a normal urgency, a high urgency, and very urgent. These factors can be combined, multiplied, or weighted to provide a priority rating. The priority of a task can be dynamically reprioritized as new tasks and workflow requests 301 are received.

In addition, each of the factors can be represented by an icon. One set of icons can represent the importance factors and another set of icons can represent the time factors. The icons can be displayed along with the workflow request 301 as a visual indication of the urgency of the tasks. In addition to icons, the task management system 200 can display shapes, colors, shading, and any other suitable symbol or combinations of symbol to provide information to the users. For example, the task management system 200 can display an icon associated with the type of task, and overlay an additional icon associated with the importance factor and a color coded symbol associated with the time factor. Similarly, icons and symbols can convey information such as completion status of a task or busy status of a user. In a configuration, tasks having normal urgency and normal importance do not use an icon or symbol in order to reduce the amount of clutter on the display and to highlight those tasks that are of a higher urgency or higher importance.

Icons or symbols can be dynamically changed based on contextual information available to the task management system 200. For example, a time factor icon can be changed from normal urgency, to high urgency, to very urgent as time progresses towards the requested completion time for the task associated with workflow request 301, while an icon for the importance factor remains unchanged. For example, a workflow request 301 can be sent at 10:00 AM with a time factor of normal urgency, or standard urgency, and a due time of 1:00 PM. The task management system 200 can be configured, for example using a rule, such that if the workflow request 301 is not acknowledged, or if performance of the associated task has not commenced, within 30 minutes of the due time 506 of the task, the urgency of the workflow request 301 and the associated task can be changed to high urgency, and at 15 minutes the urgency can be changed to very urgent. The change in urgency can trigger the pop-up alert window, the audible alert, the vibratory alert, and force the second user to acknowledge or otherwise respond to the workflow request 301. Similarly, the urgency can dynamically change based on other factors such as external events including environmental factors, events reported by sensors, milestone events such as commencement of performance of a task, completion of related tasks in the workflow by the user or other users, personnel shift changes, and so forth. The task management system 200 can use this priority in ordering the presentation of tasks displayed from a user's task queue 1102 illustrated in FIG. 11.

Figure 7:
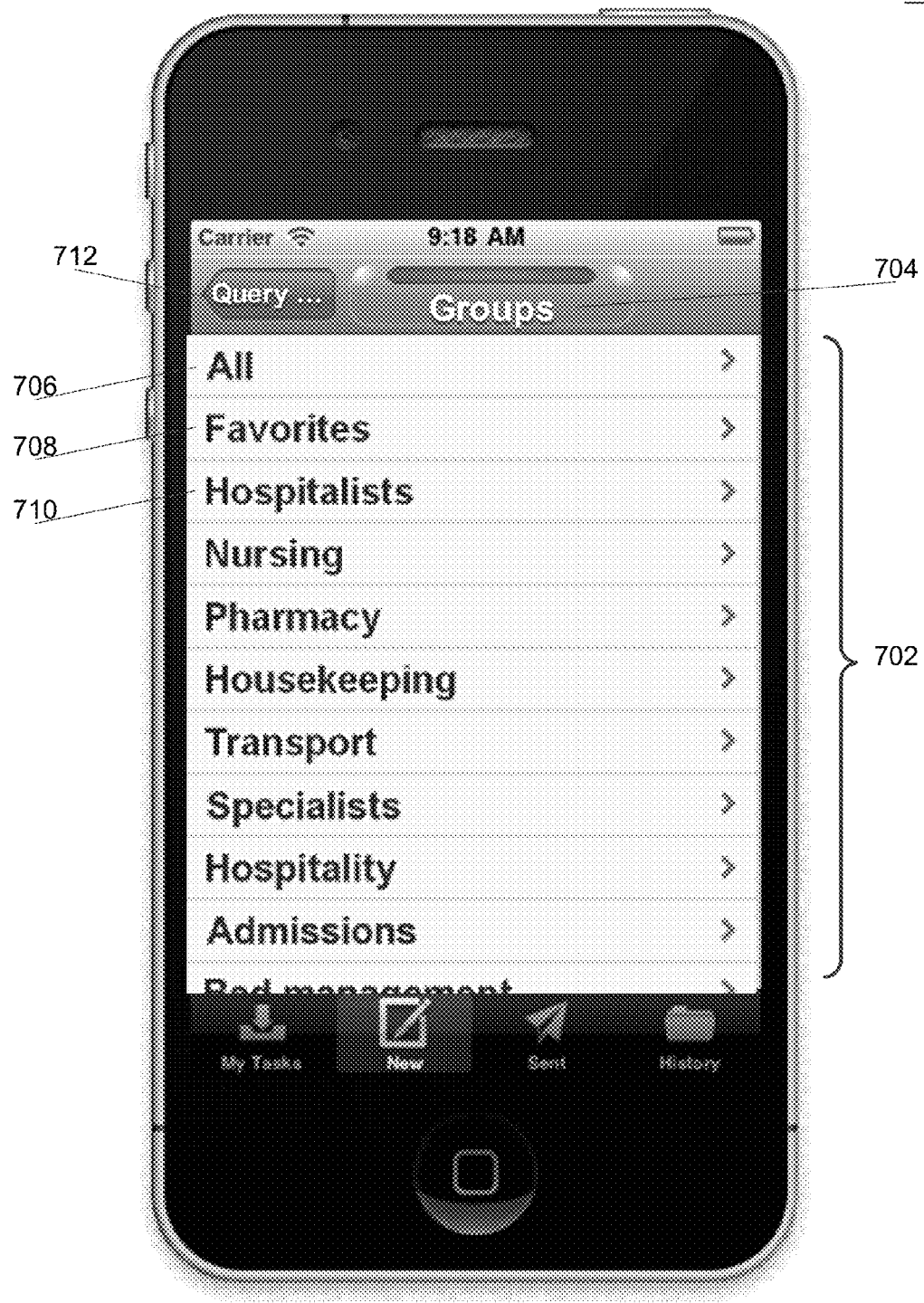
Figure 8:
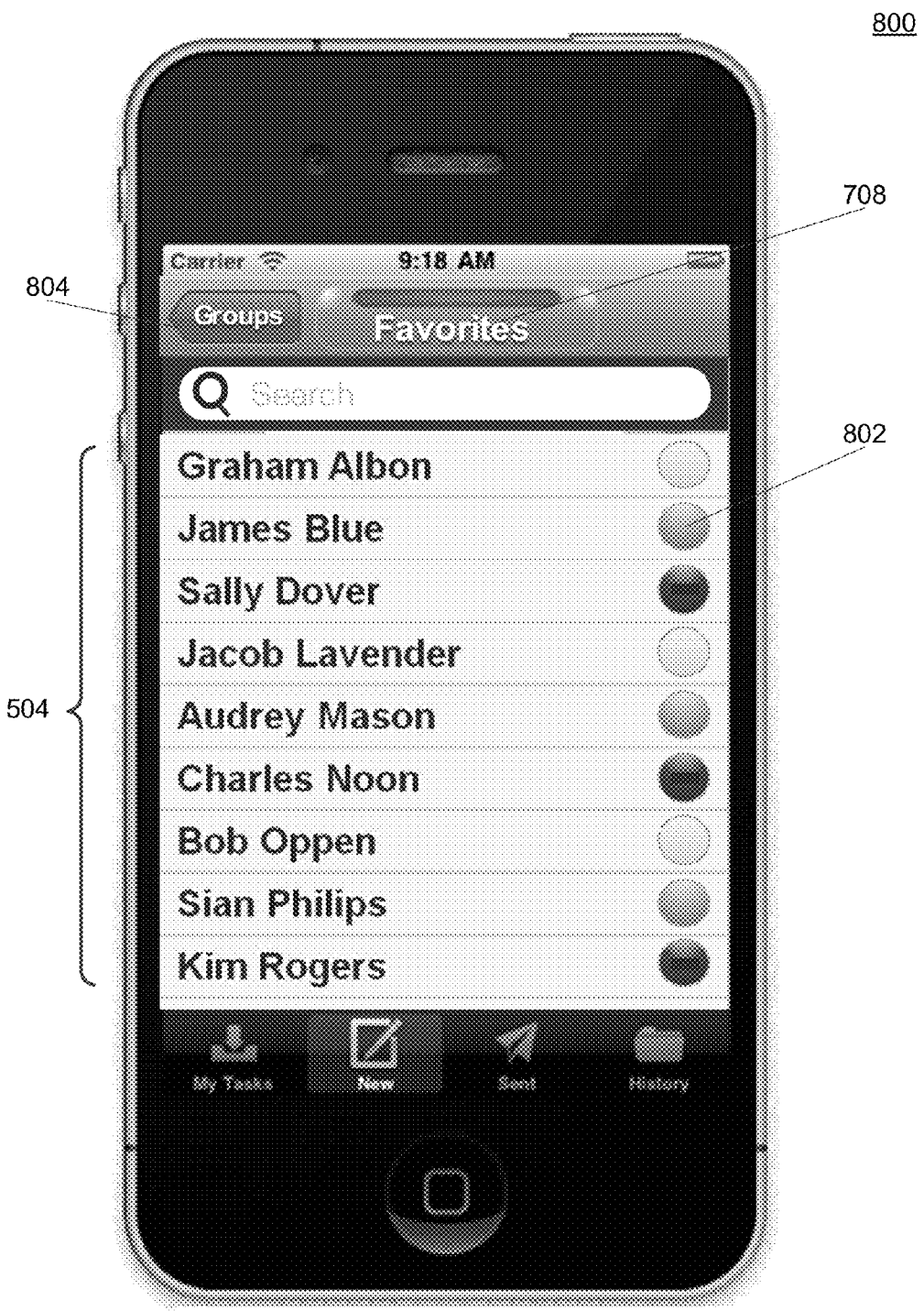

Referring now also to FIGS. 7 and 8, screenshots 700 and 800 illustrating selection of the contact address 504 are presented. The first user's address book 702 can be organized into groups 704, for example the groups all contact addresses 706, favorites 708 or recently used contact addresses 504, nursing 710, and so forth. The first user can select one of the groups 704 to drill down to individual contact addresses 504, or press the back selection 712 to return to the screen for creating a new workflow request 301 shown in screenshot 400. If the first user selects one of the groups 704, for example the favorites 708 selection, they are presented with screenshot 800 that presents contact addresses 504 associated with that group 704. Referring to FIG. 8, contact address 504 associated with the group 704 called favorites 708 is presented. Each of the contact addresses 504 can include an icon or status identifier 802. The status identifier 802 can provide, at a glance, information about the availability of the user associated with the contact address 504. Example status identifiers 802 can include color identifiers such as green, yellow, red, blue, and so forth that identify whether the user associated with the contact address 504 is available to accept new workflow requests 301, is busy performing a task, is available or unavailable for incoming communication requests, is currently in a communication session with another user, has turned off their mobile computing device or is out of range, and so forth. The status identifier 802 can be configured by the task management system 200. The status identifiers 802 can indicate the relative amount of tasks and workflow requests 301 in the user's task queue 1102. The status identifiers 802 can be solid colors, shaded or have markings, include symbols, include overlapping icons, be flashing, or use other suitable techniques for conveying status information. If the first user does not select a contact address 504, the first user can select the back selection 712 to return to the address book screen. The back button 804 can display contextual information about the display or screen that the first user will return to upon pressing the back selection 804. In a configuration, the first user can select the status identifier 802 of a contact address 504 to receive additional information about the status of that user.

Figure 9:

The first user can select the contact address 504 to use for the communication. Referring now also to FIG. 9, a screenshot 900 of a contact address 504 is presented. The screenshot 900 presents the name 902 of the user that is associated with the contact address 504, which can be different from, or the same as, the text used in the contact address 504 itself. In a configuration, the first user can modify the text of the contact address 504 to make the contact address 504 more user friendly, for example using a nickname for a user. In addition to the name, there can be several different options for communicating with the second user that is associated with the contact address 504. For example, the contact address 504 can include a mobile phone number 904, an office phone number 906, an email address (not shown), a home phone (not shown), and other suitable contact addresses 504. The contact address 504 can also include additional information 910 about the user associated with the contact address 504, such as groups the user is associated with and titles, positions, or roles performed in the workplace.

In the configuration illustrated in the screenshot 900, only some of the possible fields are illustrated. This can be done to comply with a business policy. For example, a business using the task management system 200 may require all users to use an IVR system 216 for receiving and responding to workflow requests 301 so that there is uniformity in how users are informed of workflow requests 301 and how they send acknowledgements and responses 303. Another example of a business policy is a privacy policy. A privacy policy may limit what kind of information of the second user is available to the first user.

In another configuration, the fields 904, 906 that are displayed can be limited to those that are populated with information. This can reduce the amount of clutter on the display and make it easier for the first user to select the appropriate field 904, 906 for sending the workflow request 301. In yet another configuration, the fields 904, 906 that are displayed can be based on context or contextual information. For example, if the task management system 200 is aware that the second user associated with the contact address 504 is currently contactable by either their mobile phone 904 or work phone 906, then the task management system 200 can limit the display to just those selectable fields 904, 906.

After the first user has selected the contact address 504 and the particular mode of communications for sending the workflow request 301 to the second user, the first user can select the back selection 912 to return to the previous screen. The back selection 912 can display information about the display or screen that the first user will return to upon pressing the back selection 912. In a configuration, the back selection 912 can use the standard navigation controls available through the operating system of the second mobile computing device.

The first user can select the contact address, for example the contact address 504 associated with the user "Anne Brown". After selecting, the user will return to the group 704 called "Nursing" 710 to display other members of the group "Nursing". In this way, the first user can select multiple contact addresses 504 for sending the workflow request 301 before returning the first user back to the screen for creating a new workflow request 301 shown in screenshot 400.

Figure 10:
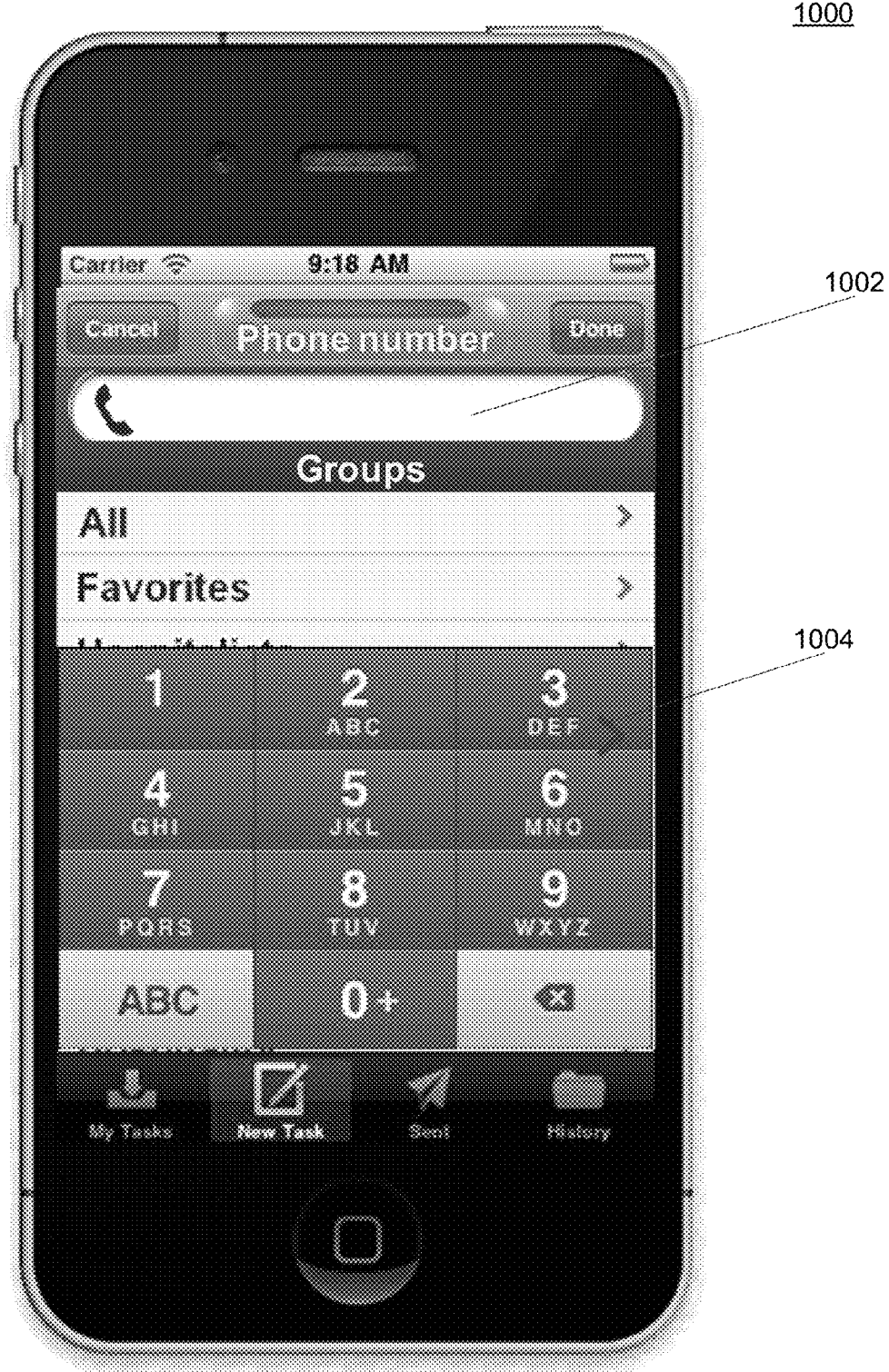

Referring now to FIG. 10, a screenshot 1000 illustrating manual entry of a contact address 504 associated with task of a workflow request 301 is presented. In addition to using the address book functionality described in FIGS. 7-9, the first user can also manually enter a contact address 504. In particular, this screenshot 1000 illustrates the entering of a phone number for a phone action task. The first user can enter the phone number 1002 using a keypad entry 1004. In a configuration of the task management system 200, the first user can enter information using other means available on the first mobile computing device 206, for example, voice recognition. In various configurations, other contact address 504 information can be entered including, but not limited to, an email address or a name. The information entered by the first user can also be used to look up an address in the address book, or to create a new contact address 504. More generally, this could be used to set the email address for launching a pre-addressed email, or embedding a web-base uniform resource locator (URL) for launching a web page.

Returning back to FIGS. 2 and 3, once the first user of the first mobile computing device 206 has created the workflow request and addresses the workflow request 301 to the contact address 504 of the second mobile computing device 208, the first user sends the workflow request 301. The workflow request 301 can be received by the workflow server 210 prior to, or in conjunction with, receipt of the workflow request 301 by the second mobile computing device 208. In FIG. 3, the timeline of operations 300 illustrates the case where the workflow request 301 is received first by the workflow server 210 and then forwarded to the second mobile computing device 208 by the workflow server 210.

The inclusion of a workflow server 210 in the communication path between mobile computing devices 206, 208 provides several benefits described below. However, in a configuration, the workflow requests 301 and subsequent communications can be sent directly between mobile computing devices 206, 208 using a peer-to-peer communication path without a workflow server 210. In another configuration, the mobile computing devices 206, 208 can send copies of messages or summary information about the workflow requests 301 and subsequent communications to the workflow server 210 and the other mobile computing device 206, 208.

One benefit of using a workflow server 210 is that the workflow server 210 can optionally validate or alter information in the workflow request 301. For example, the workflow server 210 can validate that the workflow request 301 is being sent to a current employee. The workflow server 210 can alter who the workflow request 301 is sent to. For example, if the intended recipient of the workflow request 301 has another user filling in for them, then the workflow request 301 can be forward to that user. The workflow server 210 can also police the workflow request 301 by verifying the workflow request 301 against one or more business policy rules or regulatory policy rules.

Another benefit of using a workflow server 210 is that the workflow server 210 can log the various messages and communications between the mobile computing devices 206, 208. In various configurations, the workflow server 210 can save copies of the messages and save information about the communications between the mobile computing devices 206, 208. In various configurations, the workflow server 210 can be used to perform analysis of the messages and communications as described below.

Another benefit of using a workflow server 210 is that the workflow server 210 can work in conjunction with a presence server to determine if the contact address 504 needs to be changed in order to send the workflow request 301 to the second user of the second mobile computing device 208. For example, if the second mobile computing device 208 is present on a local WiFi intranet, an example of a private network 204, the workflow server 210 can send the message using an email message. However, if the second mobile computing device 208 is present only on a public network 202 such as a cellular network and the second user does not have a data plan for the second mobile computing device 208, then the workflow server 210 can send the workflow request 301 to the second user's mobile computing device 208 using the short message service (SMS), for example by instructing the second user of the second mobile computing device 208 to dial into the IVR 216 to receive and respond to the workflow request 301.

The workflow server 210 forwards the workflow request 301 to the second mobile computing device 208. The second user of the second mobile computing device 208 receives the workflow request 301 and can present the workflow request 301 to the second user. The workflow request 301 can be presented to the second user in multiple different ways. For example, the workflow request 301 can be presented on a human-machine interface such as a display on the second mobile computing device 208. A display is only one type of output device 170 of a computing device 100. The workflow request 301 can also be presented as an auditory message, for example using a text-to-speech feature, by playing a sound file, such as a .wav, .mp3, or other auditory means.

The workflow request 301 can be presented with an alert, such as a visual alert on the display, a vibratory alert, an audible alert, or a combination of alerts. The workflow request 301 can be presented as a combination of an alert and a displayed message. These presentations and alerts can alert the second user that a new workflow request 301 has been received and can provide information to the second user about the type of, urgency of, or importance 508 of, workflow request 301. For example, the second user may carry their second mobile computing device 208 in a pocket. For example, the combination of a vibratory alert, and an audible alert particular to the kind of task in the workflow request 301 can immediately alert the second user to the type of workflow request 301.

The workflow server 210 can send a workflow request 301 to the second user using one or multiple methods, including but not limited to using an IVR system 216, an email, a text message, instant messaging, and multimodal communications among other methods. The second user can be notified about a new workflow request 301 or change to an existing task or workflow request 301 which then triggers the second mobile computing device 208 to poll the workflow server 210 to receive the workflow request 301. The workflow request 301 can be received in an XML message, for example if the task management system uses RESTFUL web APIs between the workflow server 210 and second mobile computing device 208. The workflow request 301 and task can include metadata for creating the communications sessions for processes with other servers such as an email server, a web server, a call server, among other servers.

In another configuration, the notification can be a SIP notification, and the workflow request 301 can be received in a SIP notification. In another example, the alert can be a call-in number associated with the workflow request 301. The alert can be sent to a second-user's pager or mobile phone to prompt the second user to call into the IVR system 216. The second user can have a personal identification number (PIN) for responding to the workflow request and the workflow request 301 can have a numeric identifier. The second user calls into the IVR system 216 and the IVR system can read out the message, for example using a text-to-speech module. The second user can speak their response to the IVR system 216 and using a speech recognition module the IVR system 216 can generate the response 303. The second user can also press number keys on a phone to send responses using the dual-tone multi-frequency (DTMF) in-band signaling used by the phone for dialing. The second user can also opt to respond to the workflow request 301 using email, text messaging, and other methods available to the second user. The task management system 200 can support multi-modal communications wherein the workflow request 301, messages, acknowledgements, responses 303, and notifications are performed using the same, or different, communication mediums.

When the second user is not reached or has not responded back with an acknowledgement or response 303, the workflow server 210 can take additional steps before escalating the workflow request 301 as described in greater detail later in the disclosure relating to server-generated workflow requests 304. For example, the workflow server 210 can make calls to the second user a preconfigured number of times using a preconfigured interval between each of the calls. The workflow server 210 can attempt to reach the second user using different mediums based on the information available to the workflow server 210 in the contact address associated with the second user. The second user can provide a preferred contact mode for the workflow server 210 to use in contacting the second user. For example, the second user can configure a preferred order of addresses, such as mobile phone number 904 and then office phone number 906, in the contact address 504 for contacting the second user.

Figure 11:

Referring now to FIG. 11, a screenshot 1100 illustrating a display of tasks from a user's task queue 1102 is presented. The display of the user's task queue 1102 can be a scrollable display of tasks. The user's task queue 1102 can be a single task queue 1102 or can include multiple task queues 1202. For example, there can be a task queue 1102 associated with tasks of a particular priority level, urgency, or importance 508. The task queue 1102 can include tasks and workflow requests 301 sorted by due date. The task queue 1102 can be an unsorted or sorted list from which the display of tasks is first prioritized and then displayed to the user. There can be a separate task queue 1102 for workflow requests 301 and separate task queue 1102 for tasks associated with the workflow requests 301 that have already been accepted by the second user.

The tasks can be prioritized using rules and combinations of rules. Example rules for prioritizing the tasks can include prioritizing by a time factor, for example based on the current time, the expiration of a timer associated with the task, a preset time or threshold time prior to the requested completion time of the task, the elapsed time since the workflow request was requested or accepted by the second user. Another example rule can include prioritizing based on a milestone event such as the start of performance of the task, the completion of the task, or the non-performance of the task. Another example rule can include prioritizing based on environmental factors such as an input from a sensor, for example a sensor on a piece of monitoring equipment, a signal from an external system, or data available to the task management system that is obtained from an information source such as an external database. Another example rule can include prioritizing based on personnel factor such as changes in available personnel, for example if a second user has quit or been terminated, a shift change such as a shift change associated with a particular time, and the availability of a second user or a group of second users for performing the task.

Another example rule can include prioritizing based on the importance 508, for example the importance 508 requested by the first user, an urgency 508 determined by the second user or an administrator, for example an importance 508 changed by the second user performing a user override function to change the importance 508, an urgency determined by the location for performance of the task, for example a location used in conjunction with the current location of the second user. In this example, if the second user is in close proximity to the location for the performance of a task, the urgency or importance 508 for that task can be temporarily increased so as to alert the second user of the task nearby that needs to be performed. Similarly, if the second user performs work in two different locations, the tasks can be prioritized so that the second user is not unnecessarily bounced between the two different locations during performance of tasks from the second user's workflow queue 1102. This is an example in which the task management system 200 can use contextual information to prioritize tasks and increase overall user efficiency. The prioritization can also be based on an urgency or importance 508 set by the type of task. Some task types can have an urgency or importance 508 set according to a business policy rule associated with the type of task or a regulatory compliance rule associated with the type of task. The business policy rule or regulatory compliance rule can use other factors in combination with the urgency or importance 508, including but not limited to, the role or position of the first user or second user, the locations of the second user or other users, the time of day, and so forth.

The second mobile computing device 208 can present an indication that there is a new workflow request 301 by displaying a numerical icon 1106 in the tasks selection 414. The second mobile computing device 208 can display the workflow request 301 in the second user's task queue 1102, or task list. In an alternate configuration, the second user must first accept the workflow request 301 before the task appears in the user's task queue 1102. The workflow request 301 can be displayed with icons 1108, 1110, colors, shading, or other indicators that provide information to the second user without requiring the second user to first select and individually view the workflow request 301. For example, the workflow request 301 can be displayed with an importance icon 1108 that shows the importance 508 of the workflow request 301, and a task type icon 1110 that provides the second user with information about the nature of the workflow request 301. The presentation of the tasks can be sorted or ordered by priority, urgency, or importance 508, by recipient name, by due time, by task type, or by another suitable field. Selecting an area of the screen, or performing a gesture such as a swipe, can trigger a popup for selecting the sorting options (not shown). In another configuration, a sort selection (not shown) can trigger the display of the sorting options.

The status of the second user can be displayed using, for example, a color indication in the status window 1112. For example, if the second user is going to begin performance of a task, the second user can quickly set their status to busy by tapping the status window 1112. The status can be selectable from a group of selections (not shown) or toggled between two states, for example an available state displayed as a green indication in the status window 1112 and a busy state displayed as a red indication in the status window 1112. The task management system 200 can use contextual information and a rule to set the status of the second user in the status window 1112 without additional input from the second user. The status window 1112 provides a visual indicator to the second user of the change in status. For example, if the second user begins performance of a particular kind of task, the task management system 200 can apply a rule and changed the status of the second user to busy and change the status window 1112 to red. When the user has completed the task, the task management system 200 can set the status of the user back to available and change the status window 1112 to green.

Figure 12:
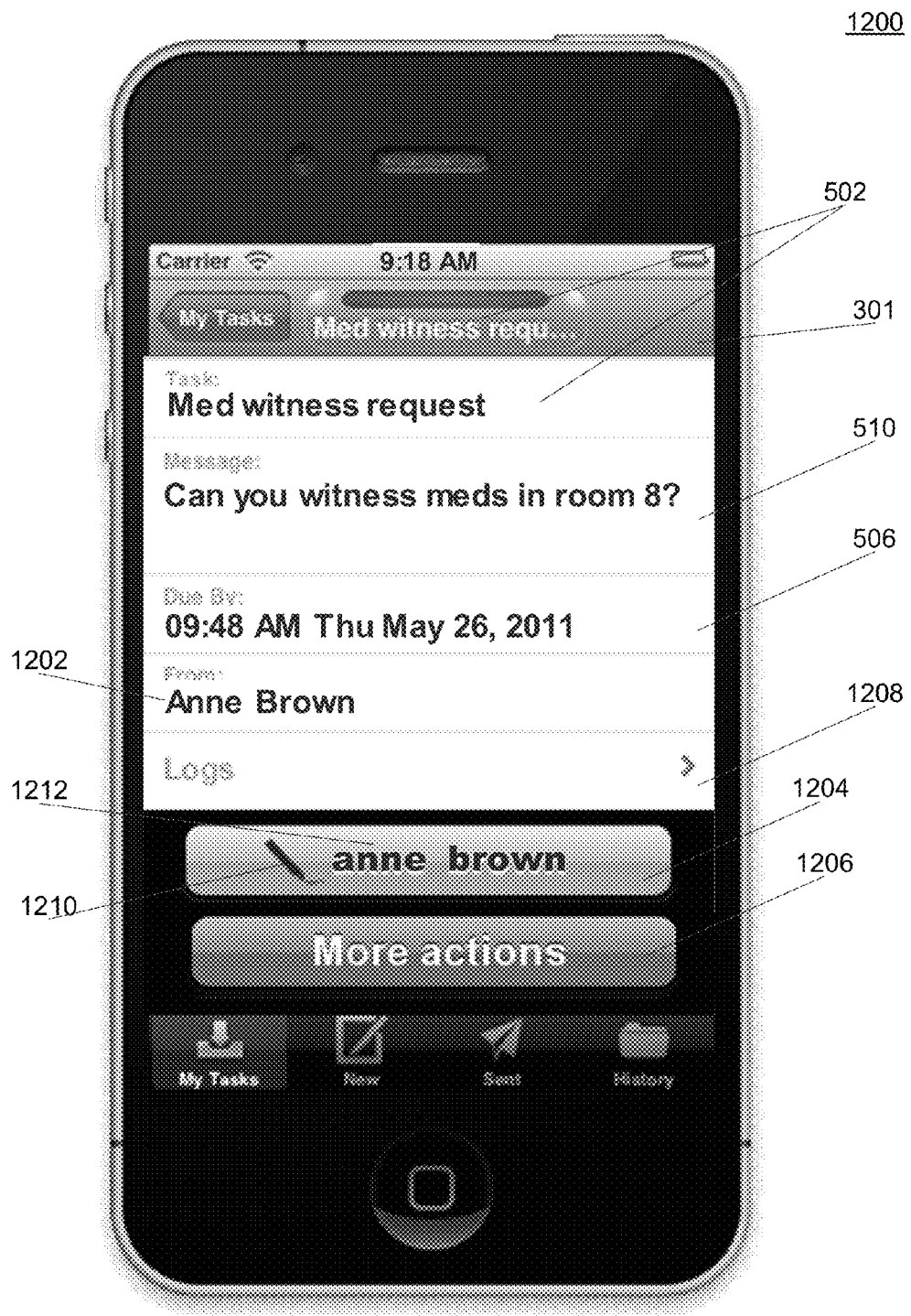

Referring now also to FIG. 12, a screenshot 1200 of the workflow request 301 is presented. The workflow request 301 includes the workflow name 502, a message 510 included with the workflow request 301, the due time 506, and the name of the first user, or sender 1202, of the workflow request 301. A log selection 1208 allows the second user to view actions, messages, and communications associated with the workflow request 301. Two action selections 1204, 1206 allow the second user to respond to the workflow request 301. The action selection 1206 opens a window of acknowledgement options 1302 to accept or reject the task.

The communication selection 1204 allows the second user to quickly open a communication session with requester 1212, such as a telephone call, an email, a message service, a proprietary messaging service, or an SMS or short message service session with the first user to discuss the workflow request 301. The sender 1202 and requester 1212 can be the same user, for example the first user as illustrated. In another example, the sender 1202 can forward a workflow request 301 that the sender 1202 received from a third user. The third user can be the user that created the original workflow request 301. In this example, the requester 1212 can be the user that created the original workflow request 301 that was sent to the first user, while the sender 1202 is the first user who received the workflow request 301 from the requester 1212. The first user can forward the workflow request 301 to the second user for performance of the task, or in other words the first user can delegate the task to the second user. The communication selection 1204 can display the requester 1212 so that in the event that the second user attempts to open a communication session 302, the second user can communicate directly with the originator of the workflow request, namely the requester 1212, and not the first user who only delegated the task to the second user.

The task management system 200 can use contextual information, such as information about the requester 1212, the sender 1202, other parties, and other information, to determine the requester 1212 that is to be displayed with the communication selection 1204. For example, if the original requester 1212 is unavailable, task management system 200 can change the requester 1212 to another user, supervisor, or help system that can assist the second user. In this way, the task management 200 can improve the user experience for the second user by displaying contextually relevant information and useful selection options to the second user.

Figure 13:

Referring now also to FIG. 13, a screenshot 1300 of the acknowledgement options 1302 is presented. The second user can select the accept selection 1304, the decline selection 1306, or by pressing the back selection 1308 the second user can defer acceptance of the workflow request 301. If the user selects the accept selection 1304, the task associated with the workflow request 301 can be marked as in progress. The task associated with the workflow request 301 can be prioritized as described above, which can change the order in which the task is displayed in the second user's task queue 1102. If the user selects the decline selection 1306, the workflow request 301 can be removed from the second user's task queue 1102. In various configurations, the workflow request 301 can be placed into the second user's task queue 1102, when it is received prior to the accept selection 1304 or decline selection 1306 and then removed if the second user selects the decline selection 1306, or the task can be placed in the second user's task queue 1102 only once the accept selection 1304 has been selected.

Referring back to FIG. 3, at point C in the first example operation 310, the second mobile computing system 208 can send a response 303 to the workflow request 301. The response 303 can be based at least in part on the selection made by the second user, and can be for example, an acceptance of workflow request 301, a rejection of the workflow request 301, and a deferring of an acceptance of the workflow request 301, among other suitable responses. The response 303 can be sent to the workflow server 210 and forwarded to the first mobile computing device 206 by the workflow server 210.

Continuing to refer to FIG. 3, at point B in the timeline of the first example operation 310, either of the first user or the second user can initiate a dialog with the other user by opening a communication session 302. For ease of explanation, point B and the communication session 302 are illustrated as occurring after the workflow request 301 has been sent to the second user at point A but before the response 303 at point C has been sent. However the communication session 302 can also be initiated prior to sending the workflow request 301, included in the workflow request 301, or initiated after the second user sends the response 303 to the workflow request 301.

The communication session 302 can be initiated by either party, and once the communication session 302 is open, the communication session 302 can comprise one or more messages sent by either party. In a configuration, text interactions and messaging can be supported natively by the task management system 200, while phone calls and other communications are initiated externally by placing calls through a call server (not shown). Also, the communication session 302 can be multi-modal and use one or more mediums, for example a text message, a multimedia message, an email message, a push-to-talk type communication session, a voice call, a video call, and a conference call. The communication session 302 can also be performed through an interactive voice response system 216 or using a web-based session based on, for example, a uniform resource locator, as appropriate. The communication session 302 can be a real-time simultaneous dialog, such as a two party voice call, a push-to-talk type communication, or a messaging type communication such as SMS or email. Some types of communication sessions 302, such as voice calls, have explicit steps of setting up a communications pathway or bearer channel, connecting the parties to that channel for the duration of the call, and then an explicit tearing down of the channel. Other types of communication do not require explicit set up and tear down steps, but can be used as needed.

By the term "open a communication session", Applicants intend the term to mean initiating an application layer use of a type of communication that permits one or both parties to communicate voice, messages, and/or data, as appropriate for the type of communication, to one another. In some instances, the communication pathway or channel exists prior to the opening of the communication session 302 and can be used by the task management system 200 as needed without setting up a separate communications pathway. For example, the task management system 200 can include a message handling module in the workflow server 210. In other instances, opening a communication session requires that a communications pathway or bearer channel be set up for the communication session 302 and then torn down at the conclusion of the communication session 302. For the purposes of this disclosure, the term opening a communication session 302 generally refers to a use of a communication protocol at the application layer, as opposed to the presentation layer, session layer, transport layer, data communication layer, network layer, data link layer, or physical layer of the seven layer Open Systems Interconnection (OSI) model. In some configurations, the task management system 200 can be implemented so as to use aspects of one or more of the layers. In some instances, the task management system 200 can be tightly integrated with the type of communications, for example by providing the messaging system for passing text messages. In other instances, the task management system 200 can make system level or application level calls to an external system, or to applications or functions, to open the communication session 302 between one or more parties. For example, voice calls can be handled by initiating the appropriate system level calls to the mobile computing device 206, 208.

Referring back to the screenshot 1200 in FIG. 12, the second user can select the communication selection 1204 to open a communication session 302 with the first user. The communication type icon 1210 displays the default type of communication and communication medium. As illustrated for the example in screenshot 1200 the default communications type can be instant messaging. The sender 1202 can specify the type of communication or allow the task management system 200 to set the default type of communication. For example, if the first user used a template to create the workflow request 301, then the default communication type can be the communication type set in the template. The workflow server 210 of the task management system 200 can apply a business policy or regulatory policy to change the communication type. For example, for regulatory purposes, some types of workflow requests 301 may require a voice communication between the parties. An example of this can be a workflow request 301 from a medical doctor or medical professional that, for purposes of insurance coverage and regulatory compliance, requires the recipient of the workflow request 301 to verbally confirm the task instructions with the medical professional.

Figure 16:

The second user can select the communication selection 1204 to make the second mobile computing device 208 open a communication session 302, 308 with the requester 1212, who can be, for example, the first user. Referring also now to FIG. 16, a screenshot 1600 of a dialog between a first user and a second user is displayed. The first user, in the workflow request 301, included a message 510 asking the second user if they could "witness meds". The second user can send a reply 1602 to the message 510 of the first user using the communication session 302. For example, in the reply 1602 the second user can negotiate a time for starting performance of the task in the workflow request 301 by typing the reply 1602 into the text input box 1604 and selecting the send selection 1606. The second user can return to the display shown in screenshot 1200 without sending a reply 1602 by selecting the back selection 1610. The second user can send a predetermined phrase 1702 by selecting the phrases selection 1608.

Figure 17:
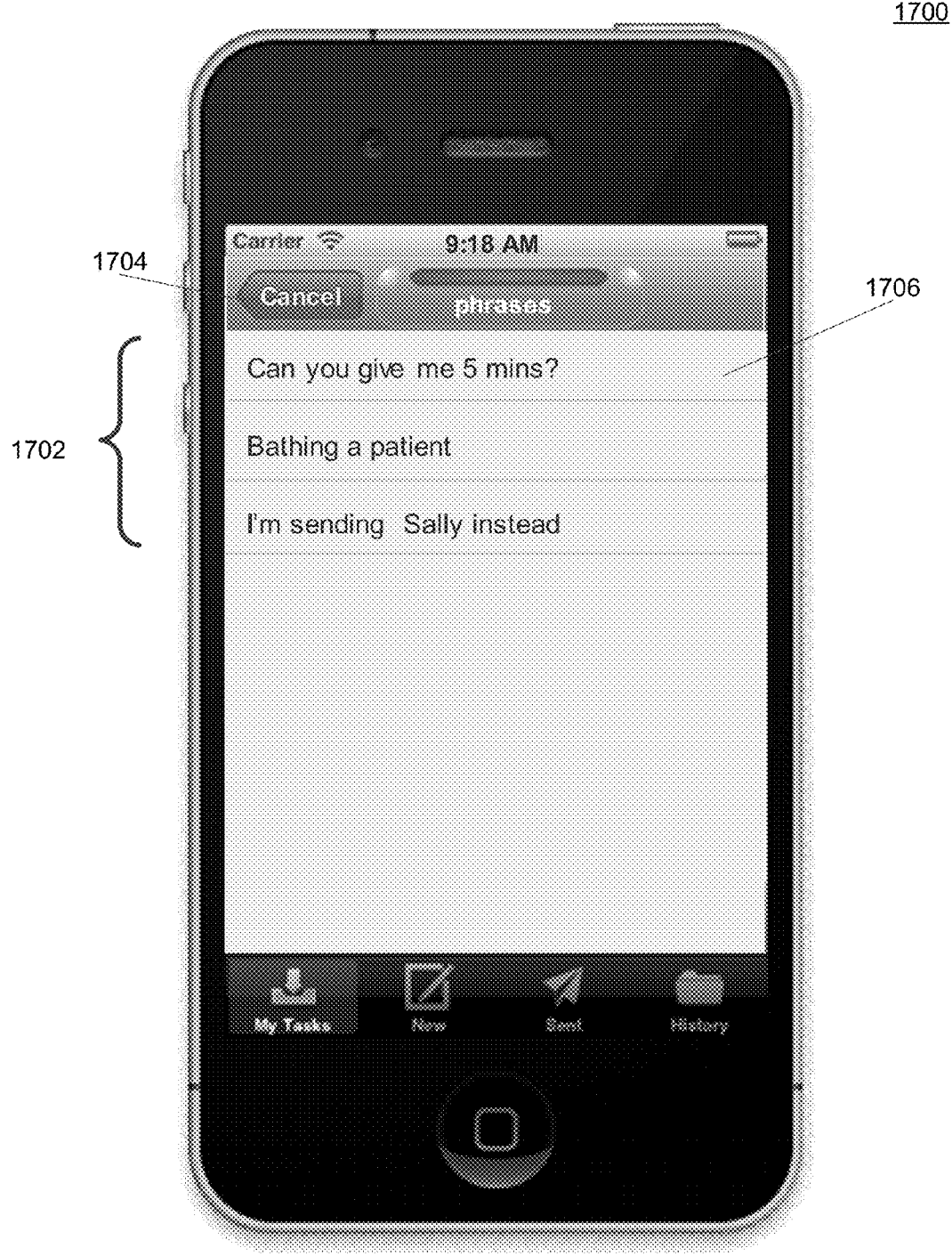

Referring also to FIG. 17, a screenshot 1700 of predetermined phrases 1702 is presented. The predetermined phrases 1702 can be preconfigured based on the workflow request 301. The predetermined phrases 1702 can be based on previous replies 1602. The second user can select the back selection 1704 to return to the dialog between the first user and the second user shown in screenshot 1600. The user can select one of the predetermined phrases 1702 to have the text of that predetermined phrase 1702 placed into the text input box 1604. For example, if the second user selects the predetermined phrase 1702 "Can you give me 5 mins?" as the selected phrase 1706, then the text of the selected phrase 1706 is placed into the text input box 1604 as illustrated in the screenshot of FIG. 18 and as described in the accompanying detailed description below.

In a configuration, the communication session 302 can be preconfigured as a structured communication session 302. After each message sent or received by a user, the predetermined phrases 1702 can be reconfigured based on factors such as the previously selected preconfigured phrase 1702, a received text or a received preconfigured phrase 1702 from the other user, an acceptance of the workflow 301, a rejection of the workflow 301, and a performance of a task associated with the workflow request 301, among other factors. The structured communication session 302 is an example of a response-sequence ordered set of messages. A structured communication 302 can be preconfigured by an administrator of the task management system 200 to facilitate the flow of the issuance of workflow requests 301, the acceptance of workflow requests 301, the messages sent in communication sessions 302, and the performance of tasks associated with the workflow request 301, among other operations. The predetermined phrases 1702 can be selected by the task management system 200 based on phrases sent in messages during previous operations and microflows.

Figure 18:

Referring also to FIG. 18, a screenshot 1800 of editing text in the text input box 1604 is illustrated. Before selecting the send selection 1606, the second user can perform a text edit 1802 of the "Can you give me 5 mins?" phrase 1706 in the text input box 1604. For example, the second user can perform a text edit 1802 to change "5" minutes to "10" minutes as illustrated in the screenshot 1800.

The workflow server 210 can log the messages sent between the mobile computing devices 206, 208 using the communication session 302. In various configurations, the workflow server 210 can save copies of the messages or save information about the communications between the mobile computing devices 206, 208. For example, if text messages are used, the workflow server 210 can save a copy of each text message. Similarly, the workflow server 210 can save copies of audio and video messages, including pictures. For voice and other streaming media, such as a call-based communication session 308, the workflow server 210 can be configured to save copies of the communications that pass through the workflow server 210. However, for communications that are performed directly between the mobile computing devices 206, 208, and that do not pass through the workflow server 210, such as voice calls, the workflow server 210 can log information about the call, such as the time of the call and the parties that took part in the call. This log information can be accessed by an administrator using an administrative computing device 214 or by users by viewing logs 1902.

Figure 19:
Figure 20:
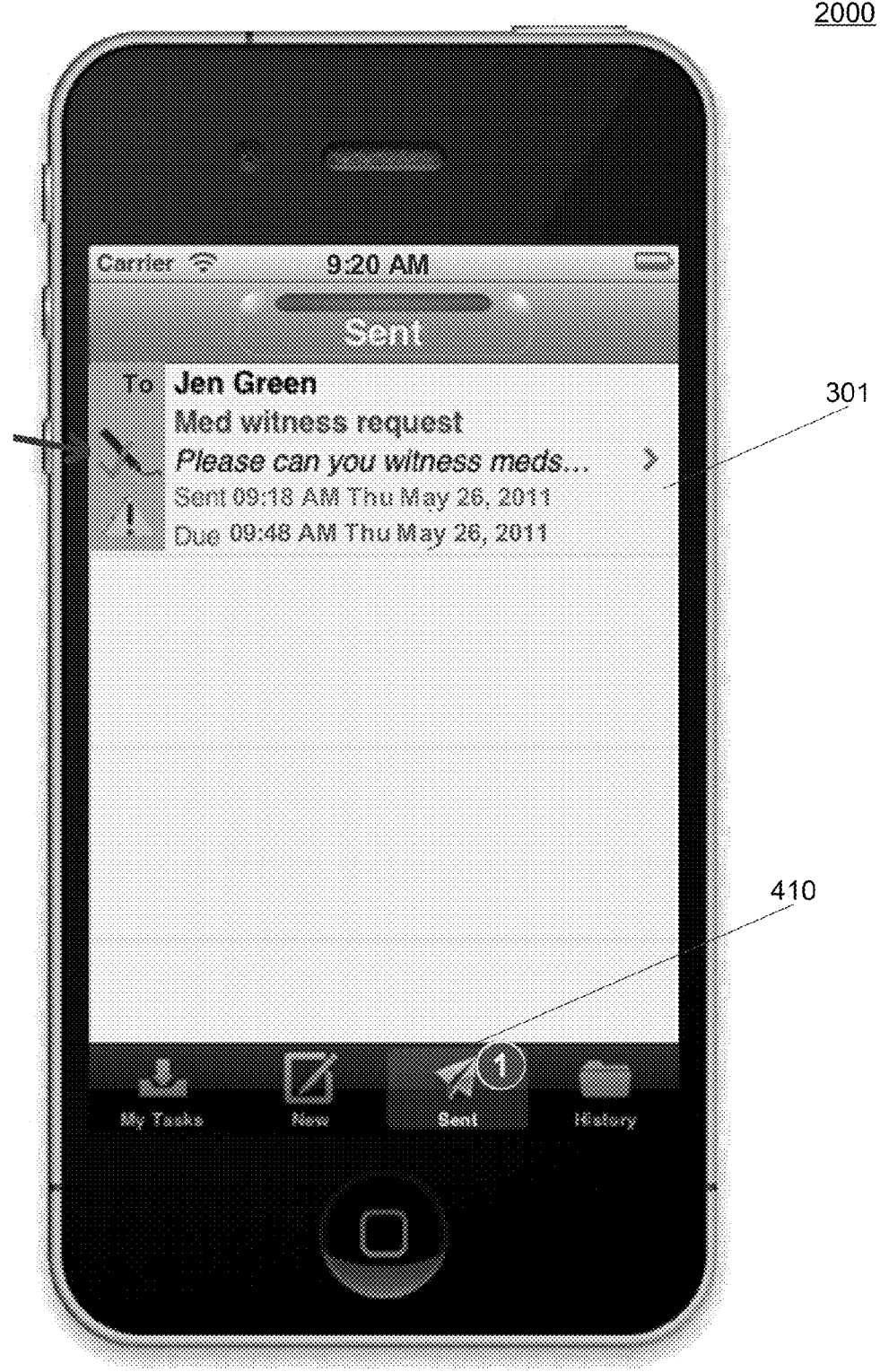
Figure 21:
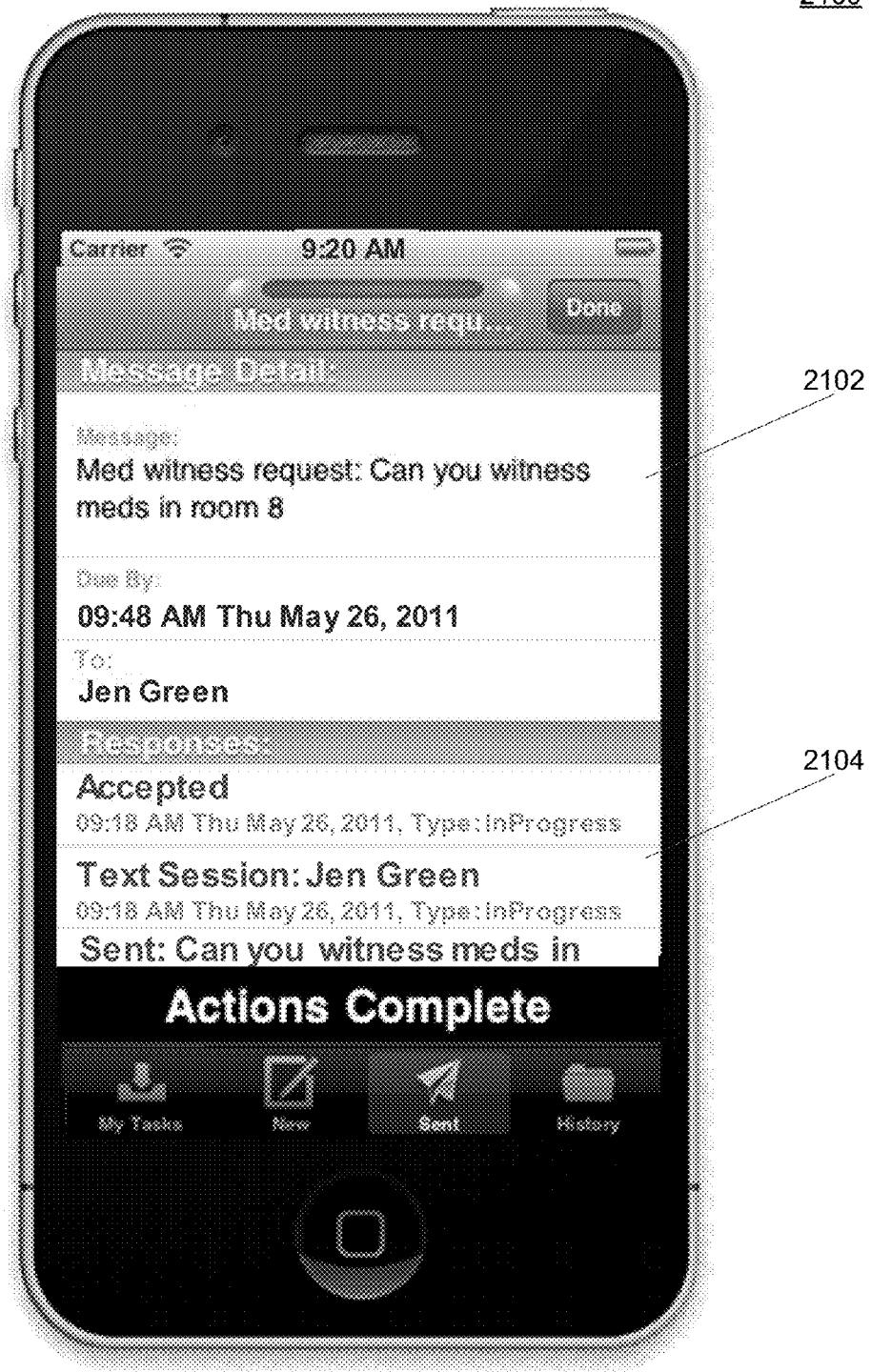

Referring now back to the screenshot 1200 of FIG. 12, the second user can select the log selection 1208 to view information about the messages, communications, and actions associated with the workflow request 301. Referring now also to FIG. 19, a screenshot 1900 of the log window is presented. The second computing device 208 can display the log 1902 of the messages, communications, and actions associated with the workflow request 301. The second user can select one of the elements from the log 1902 to view additional details (not shown). Referring now also to FIG. 20, a screenshot 2000 of the sent window is presented. The first user can select the sent selection 410 to view workflow requests 301 that the first user sent to the second user and other users. By selecting one of the workflow requests 301, the first user can view information about the workflow request 301. Referring now also to FIG. 21, a screenshot 2100 of the sent item log is presented. The first user can view information about the workflow request 301 including the message detail 2102 and the log 2104 associated with the workflow request 301.

Continuing to refer to FIG. 3, in a second example operation 320, at point D in the timeline, the workflow server 210 creates a server-generated workflow request 304 to be performed by the user of the second mobile computing device 208. The second user can select a response 303 at point C in the timeline and send that response 303 back to the workflow server 210. Example server-generated workflow requests 304 include those generated by recurring timers, for example daily tasks that need to be performed, and those generated by expiration of timers, including those related to tasks that are due or overdue. The workflow server 210 can send a server-generated workflow request 304 based on a threshold event, such as an approaching due time.

Another example server-generated workflow request 304 can be an escalation request associated with a workflow request 301. The task management system 200 can send the escalation request to members of a group, for example a group of users that perform a similar role or function as the second user. For example, if the second user is a nurse in a hospital, then the escalation request can be sent to other nurses on the same shift to see if one of those nurses is available to perform the task associated with the workflow request 301.

There can also be multiple escalating tiers of escalation requests. If a workflow request 301 is not accepted, or if the task associated with the workflow requests 301 is not performed within a threshold amount of time, then the workflow request 301 can be escalated to another user or group, for example a supervisor. If the workflow request 301 is still not accepted, or the task associated with the workflow requests 301 is still not performed, then the workflow request 301 can be sent back to the first user, or an alert can be sent back to the first user. Similarly, at any step in the escalation process, alerts and notifications can be sent to the first user, the second user, groups, supervisors, an administrator, and so forth.

Figure 14:
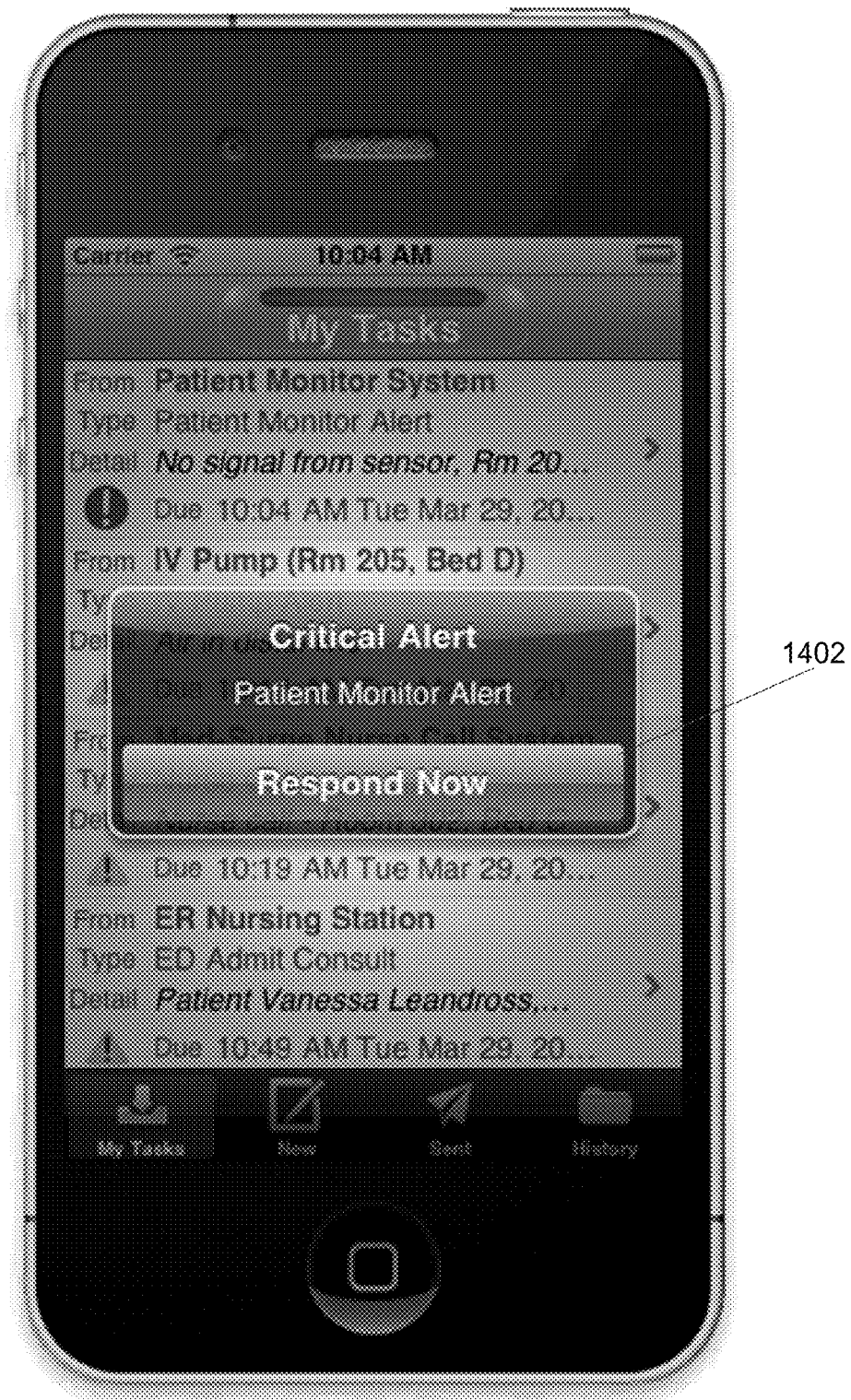

The server-generated workflow request 304 can be bidirectional, requiring the second user to send that response 303 back to the workflow server 210. The workflow server 210 can send a server-generated workflow request 304 that presents an alert 1402 to the second user based on a triggering event. A trigger can be caused by an external event, such as a sensor reading. The server-generated workflow request 304 can be a message or notification that triggers an alert 1402 by changing the urgency or importance 508 of a workflow request 301. Referring now to FIG. 14, a screenshot 1400 of an alert 1402 is presented. The workflow server 210 can send the alert 1402 to second mobile computing device 208 that can be presented to the user on the display of the second mobile computing device 208. In various configurations, the alert 1402 can be generated different ways, for example by a timer in the second mobile computing device 208, by a signal received from a sensor, by a reprioritization of a task or workflow 301 by the first user or the workflow server 210, and so forth.

Referring again back to FIG. 3, the server-generated workflow request 304 can also be a unidirectional request that does not require a response 303 from the second user. For example, if the second user has not responded to a workflow request 301, the server-generated workflow request 304 can rescind the workflow request 301 and remove it from the workflow queue 1102 of the second user. The server-generated workflow request 304 can also remove a task from the workflow queue 1102 of the second user. These operations can be performed, for example, to assign the task to a second user. After rescinding the workflow request 301 or removing the task from the user's workflow queue 1102, the workflow server 210 can send the workflow request 301 to another user.

The server-generated workflow request 304 can also place tasks directly into the workflow queue 1102 of the second user, without sending a request 301, 304 and then waiting for the second user to review and send a response 303. This can reduce the number of requests 301, 304 and responses 303 for mandatory and periodic tasks routinely assigned to, and accepted by, the second user. Similarly, these functions can be performed by a first user under certain conditions. For example, the first user can rescind a workflow request 301 that the first user created, or remove the task associated with the workflow request 301 from the queue of the second user, for example to send the task to another user using a workflow request 301. In a configuration, a first user that has supervisory privileges or administrative privileges can place or remove tasks directly into the workflow queue 1102 of a second user.

Referring back to FIGS. 2 and 3, another example of a server-generated workflow request 304 is a workflow request that is created by an administrator using an administrative computing device 214. The administrative computing device 214 can be directly connected to the workflow server 210, or networked to the workflow server 210 across a network 202, 204. In this configuration, the workflow request is a server-generated workflow request 304 because it is sent directly from the workflow server 210 to a user's mobile computing device 206, 208. In a configuration, the administrative computing device 214 can also send workflow requests 301 to the workflow server 210 as described for example by operation 310.

Continuing to refer to FIG. 3, in a third example operation 320, at point A in the timeline, the first user of a first mobile computing device 206 creates a workflow request 301 having a task to be performed by a second user of a second mobile computing device 208. The workflow request 301 is sent to the workflow server 210 to be forwarded to the second mobile computing device 208. At point E in the timeline, the workflow server 210 can create a rule-based response 305 for the second mobile computing device 208 that is sent to the first mobile computing device 206. The rule-based response 305 can be an acceptance, and a rejection, among other suitable responses. If the workflow server 210 accepts the workflow request 301, the workflow server 210 can add the workflow request 301 or the task associated with the workflow request 301 to the workflow queue 1102 of the second mobile computing device 208. If the workflow server 210 rejects the workflow request 301, both the first mobile computing device 206 and the second mobile computing device 208 can receive a notification of the rejection. The basis for the determination of whether to accept or reject the workflow request 301 can be based on contextual information available to the workflow server 210 and the application of a rule. An example of a rule is to reject a workflow request 301 if the second user is currently busy performing a task and has a workflow queue 1102 filled with tasks that would prevent the second user from performing the workflow request 301 by the required time. Rules can be created by an administrator using the administrative computing device 214 and configured to be applied in a desired order.

In an example, the second mobile computing device 208 can be powered off, out of range for accepting communications, or can be logged out of the task management system 200. The second user of the second mobile computing device 208 can also alert the task management system 200 that the user is currently busy, for example if the user is performing a task or has set their status to busy or unavailable. This status setting, or availability setting, permits the second user to set their current availability for receiving workflow requests 301, messages, and calls to busy or unavailable. The availability setting of the user can work in conjunction with the urgency or importance 508 setting to permit the task management system to use context specific rules and information about the workflow requests 301, messages and calls to determine whether to allow incoming workflow requests 301, messages, and calls to interrupt the second user. For example, if the second user has set their second mobile computing device 208 to busy, so as to not receive further workflow requests, messages, and calls, the workflow server 210, second mobile computing device 208, or another portion of the task management system 200 can use a rule to determine whether to override the availability setting set by the user. For example, this rule can be based at least in part on contextual information about the reason the first user is busy, as well as the urgency or importance 508 and type of workflow request, message, or call.

In an example, if the first user is a hospital professional and has their availability set to busy during a consultation with a patient so as to not be interrupted, then a rule may allow a workflow request 301 that includes code blue emergency and that has an urgency or importance 508 of a high enough level to override the busy availability setting of the first user and alert the first user to the workflow request 301. In another example, during performance of a task from the second user's workflow queue 1102, a rule can temporarily set the availability status of the second user to busy, depending on the task, in order to minimize interruptions during performance of the task. By providing contextual information about the task being performed and applying that information to incoming communications using configurable rules, an administrator can configure the communication aspects and task management aspects of the task management system 200 to match the needs of the workplace, without burdening the users with multiple screens of individual configurations.

Figure 15:

Referring now to FIG. 15, a screenshot 1500 of current status options 1502, 1504 for the user's availability setting is presented. The second user of the second mobile computing device 208 can select the logout selection 1502 to log out of the task management system 200. The second user can also select the busy selection 1504 to send an indication to the task management system 200 that the user is currently unavailable. Selecting the busy selection 1504 can also change color presented in the status window 1112 as described in the detailed description accompanying FIG. 11. The task management system 200 can use contextual information to determine the current status of the second user and use that information to make a determination about whether to accept or reject a new workflow request 301 for the second user. The task management system 200 can also use contextual information to determine whether to instead forward the new workflow request 301 to the second user for a decision. The task management system 200 can delay sending the workflow request 301, based on a rule, to avoid interrupting the second user during the performance of a task. In this instance, the task management system 200 can delay sending the workflow request 301 until the second user has updated their status to available. In an example, the task management system 200 can use information about a previous performance of a particular task in determining how long on average the second user will be busy with the current task. Then, based on that average time, a rule can be applied to determine whether to respond to the workflow request 301 for the user, or wait for the second user to make the decision whether or not to accept the workflow request 301.

In another example, if the second user just accepted a workflow request that is of a time sensitive or urgent nature, for example if the second user is a hospital professional responding to a code blue, then the task management system 200 can apply a rule to reject or accept new incoming workflow requests 301 without interrupting the second user. An example rule can be to accept, or delay sending, a server-generated workflow request 304 for a daily operation that is not time sensitive, and that is normally accepted by the second user, when the second user is currently busy responding to a workflow request 301 having an importance 508 of very important or an urgency that indicates immediate action is required. For example, if the second user is responding to a code blue workflow request 301, then the workflow server 210 can either accept the server-generated workflow request 304 or delay sending the server-generated workflow request 304. In another example, if a workflow request 301 that is time sensitive is received by the workflow server 210 and addressed to the same second user in the previous example, the workflow server 210 can apply a rule to reject the workflow request 301 on behalf of the second user when the contextual information available to the task management system indicates that the second user will have insufficient time to perform the task by the desired time.

The workflow server 210 can also use one or more business policies to determine whether to accept, reject, or reassign workflow requests 301. For example, if the second user has a workflow queue 1102 having unperformed tasks above a configurable threshold, the workflow server 210 can apply a business rule and send a reject response 304 for the second user. Also, the workflow server 210 can perform operations to distribute workflow requests equally between members of a group. For example, if the second user is a member of a group that can share assignments, then upon receiving workflow requests 301 addressed to the second user, the workflow server 210 can check the workflow queues of the members of that group and change the recipient of the workflow request 301, if necessary, to distribute work more evenly between members of the group.

The task management system 200 can use contextual information to improve the user experience of users of the mobile communication devices 206, 208 in multiple ways. In an example similar to the one presented above, the task management system 200 can apply a rule and respond to workflow requests 301 for users when appropriate. This not only reduces the number of key presses or selections that the users would otherwise have to make, but it also speeds up the process of the assignment of, and ultimately the performance of, workflow requests 301. When a first user sends a workflow request 301 to a second user who is busy or unavailable, permitting the workflow server 210 to make a rule-based response with a decline notification quickly alerts the first user that the second user is busy or unavailable. This information about the status of the second user permits the first user to immediately send the workflow request 301 to a different user. Without the response provided by the workflow server 210, the first user could have to wait for a period of time for a response 303 from the second user further delaying the possibility of another user performing the task in the workflow request 301 for the first user.

Figure 22:

Continuing to refer to FIG. 3, in a fourth example operation 340 the first user of the first mobile computing device 206 can inquire about the status of a workflow request 301. At point F in the timeline, the first user creates an inquiry 306 similar to a workflow request 301. The inquiry 306 can reference a previous workflow request 301. Referring also now to FIG. 22, a screenshot 2200 of an inquiry is presented. The inquiry 306 can include a selectable response action 2202, for example to call the first user using a preferred medium for communication, in this case a voice call to the phone number 2208 of first user. The response action 2202 can include a response type icon 2206 identifying the type of action and preferred medium. The inquiry 306 can include a message 2204, for example a text message. The message 2204 can help to later identify the purpose of the response action 2202 in the log 1208. If the response action 2202 is a call, and if the contents of the call are not recorded by the task management system 200, then the message 2204 can be a good way of providing information for identifying the purpose of the call at a later point in time. The message 2204 also provides the second user with an indication of the kind of information the first user expects to receive by way of the response action 2202, thereby allowing the second user to prepare or retrieve the necessary information.

Figure 23:

The second user receives the inquiry 306 in similar fashion to a workflow request 301 as described above. The second user is presented with acknowledgement options 2302 appropriate for sending a response 307 to the inquiry 306. Referring now to FIG. 23, a screenshot 2300 of selectable acknowledgement options 2302 is presented. The acknowledgement options 2302 can include, for example, a decline selection 2304, a defer action selection 2306, and a perform action selection 2308. The task management system 200 can use the response action 2202 of the inquiry 306 in FIG. 22 to change the text of the defer action selection 2306 and the perform action selection 2308. These context-based changes to the defer action selection 2306 and the perform action selection 2308 present the second user with a more user friendly and informative display. A back selection 2310 permits the second user to return to the screen displaying the inquiry 306 shown in screenshot 2200. A back selection on the top bar 2312 returns the second user to the display of the user's task queue 1102.

Continuing to refer to FIG. 3, in a fifth example operation 350, at point H in the timeline, one of the users can open a communication session 308 with another user, for example to discuss a task prior to commencing performance of the task, during performance of the task, or after performance of the task. The communication session 308 can be in response to the inquiry 306 presented in FIGS. 22 and 23 and the accompanying detailed description. The communication session 308 can be in addition to an inquiry 306, or the communication session 308 can be in place of the inquiry 306. The communication session 308 can be similar to the communication session 302. For purposes of illustration only, the communication session 302 is displayed as one or more messages, for example text messages, that pass through the workflow server 210; the communication session 308 is displayed as a voice call between the first mobile computing device 206 and the second mobile computing device 208 that does not traverse or pass through the workflow server 210. Communication sessions 302, 308 are illustrated this way for purposes of illustration only. In various configurations, either or both communication sessions 302, 308 can be message-based such as text-based messaging, or voice-based such as POTS (Plain Old Telephone Service), cellular, WiFI, or VoIP-based (Voice over Internet Protocol), or combinations thereof. In various configurations, the communication sessions 302, 308 can be point-to-point or traverse the workflow server 210, independent of whether they are text-based or voice-based communications.

Figure 24:

Referring now to FIG. 24, a screenshot 2400 of a popup list 2402 for opening a communication session 308 is presented. In this example, the second user selects a workflow request 301 and then selects the initiate communications icon 2404 for that workflow request 301. The task management system 200 uses contextual information to populate the popup list 2402 with selectable options for opening the communication session 308. In this case, the popup list 2402 includes options for opening a communication session 308 to discuss the task in the workflow request 301 based on the communication mediums supported by both the first user and second user. The second user can select the discuss task selection 2406 using messaging, or the discuss task selection 2408 using a voice call. Each of the discuss tasks selections 2406, 2408 include a communication type icon 2410 that indicates the type of medium used in the displayed discuss tasks selections 2406, 2408. The second user can select the back selection 2412 to avoid opening a communication session 308.

In a configuration, the popup list 2402 can exclude display task selections for particular communication mediums using rules based on business policies or regulatory rules. The popup list 2402 can further exclude communication mediums based on the availability of the first user using a particular communication medium. For example, if the first user is currently on a voice call, the discuss tasks selection 2408 using a voice call can be disabled nor not displayed. In a configuration, an icon or other identifier such as color or symbol can be used to identify the status of a communication medium for the first user, but allow a second user to call the first user even when the first user is currently on another call.

Figure 25:
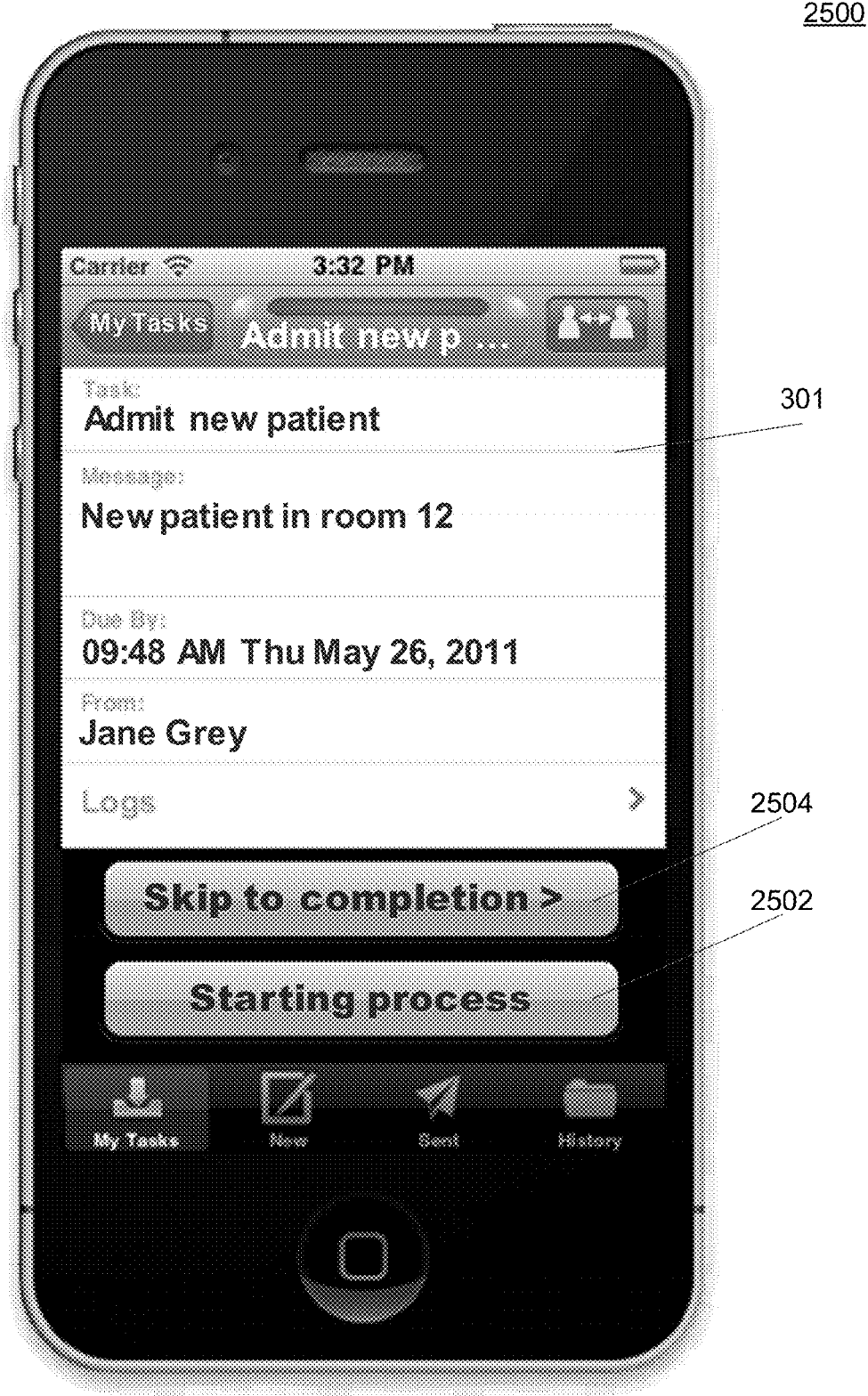

Continuing to refer to FIG. 3, in a sixth example operation 360, at point I in the timeline, the second user can send a status message 309 to the first user. An example status message 309 is a message that indicates that the second user has commenced performance of a task associated with a workflow request 301. Referring now to FIG. 25, a screenshot 2500 of a task is presented. The second user can select a status update selection 2502. The task management system 200 can display contextually relevant options for the status update selection 2502. For example, if performance of a task has not been commenced, then the status update selection 2502 can be "starting task" or "starting process" as illustrated. The text displayed can be based on the type of workflow request 301. Other types of status updates are also possible.

A status message 309 can provide an indication that a single task of a multi-task workflow request or microflow is complete. A single workflow request 301 can comprise multiple individual steps, tasks, or operations. The steps, tasks, or operations can involve other users. The steps or operations can create new tasks or new workflow requests 301 for the second user or other users. The steps or operations can be cascaded, where the completion of one task spawns another new workflow request 301. The steps or operations can be nested, where during the performance of a task a new workflow request 301 is generated and completed before performance is completed for the current workflow request 301. At each step or operation, the available contextually relevant options that are displayed for the second user can change based, for example, on the previously performed tasks, complete workflows, or messages to other users.

Continuing to refer to FIGS. 3 and 25, in a seventh example operation 370, at point J in the timeline, the second user can send a completion status message 311 to the first user. An example completion status message 311 is a message that indicates that the second user has completed performance of a task or the tasks associated with a workflow request 301. Another example completion status message 311 is a message that indicates that the second user has not completed performance of the task associated with the workflow request 301. For example, the second user may not have had time to complete the task, the task may be impossible to complete or no longer necessary to complete, the task may have been assigned or delegated to another user, for example if a shift change occurred, or can be another suitable completion status message 311.

Figure 26:
Figure 27:
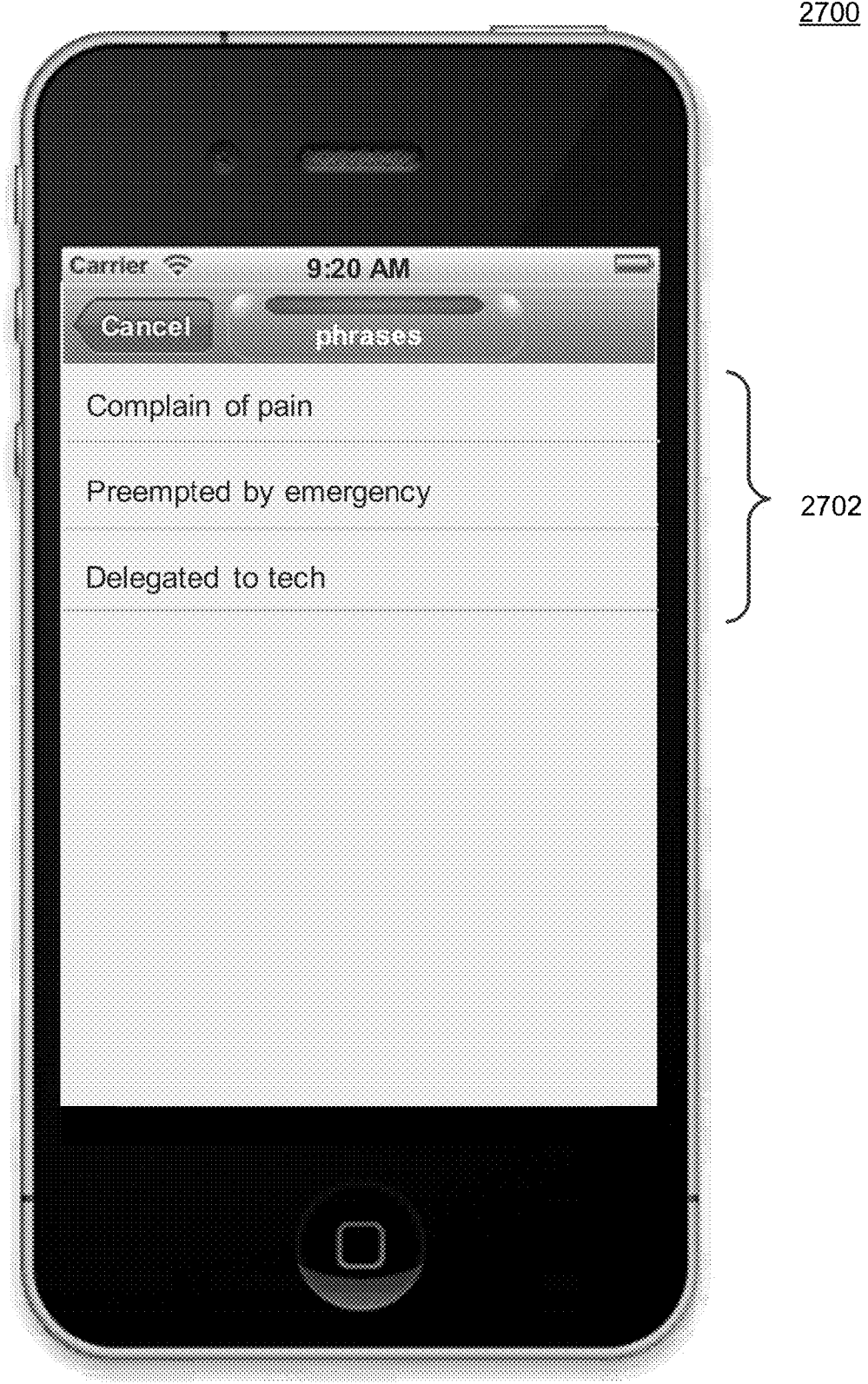

Referring again to FIG. 25, the second user can select completion update selection 2504 to display a list of completion option selections 2602. Referring also now to FIG. 26, a screenshot 2600 of a list of completion option selections 2602 is presented. The selectable completion option selections 2602 can include a done selection 2606 to indicate that the task associated with the workflow request 301 has been performed and completed successfully, and a cannot assist selection 2604 to indicate that the second user can no longer assist in performance of the task associated with the workflow request 301. A back selection 2610 permits the second user to return to the task screen without selecting a completion option selection 2602. An optional note box 2608 permits the second user to explain the reasons for not completing the task or to provide additional information to the first user. Referring also now to FIG. 27, a screenshot 2700 of a list of predetermined completion phrases 2702 is presented. The predetermined completion phrases 2702 permits the second user to select commonly used explanations that are inserted into the optional note box 2608. The predetermined completion phrases 2702 can be edited once they are in the optional note box 2608. The second user can save the current text in the optional note box 2608 as a new predetermined completion phrase.

Referring again to FIG. 3, at point K in the timeline of the seventh example operation 370, the workflow server 210 can send one or more completion messages 312 to the first user and the second user. The completion messages 312 can, for example, remove the workflow request 301 from the user's task queue 1102 among other suitable operations. The completion messages 312 can also place log information in the log 1208 of each of the mobile computing devices 206, 208. The completion messages 312 can also request copies of messages and other log information from each of the mobile computing devices 206, 208.

The workflow server 210 can send one or more completion messages 312 based on contextual information available to the workflow server 210. For example, if a workflow request 301 was created to reset a malfunctioning air exchanger, and the workflow server 210 receives information from a sensor that the air exchanger is back online, then the workflow server 210 can determine that the task associated with the workflow request 301 has been completed and send one or more completion messages 312 to the appropriate user. The workflow server 210 can also request a confirmation from the technician, for example by sending an inquiry 306 as described for fourth example operation 340, prior to marking the task as completed and sending the completion message 312. By using this available contextual information, the task management system can reduce the number of unnecessary escalations where the user has simply failed to report that the task associated with the workflow request 301 has been completed.

Figure 28:
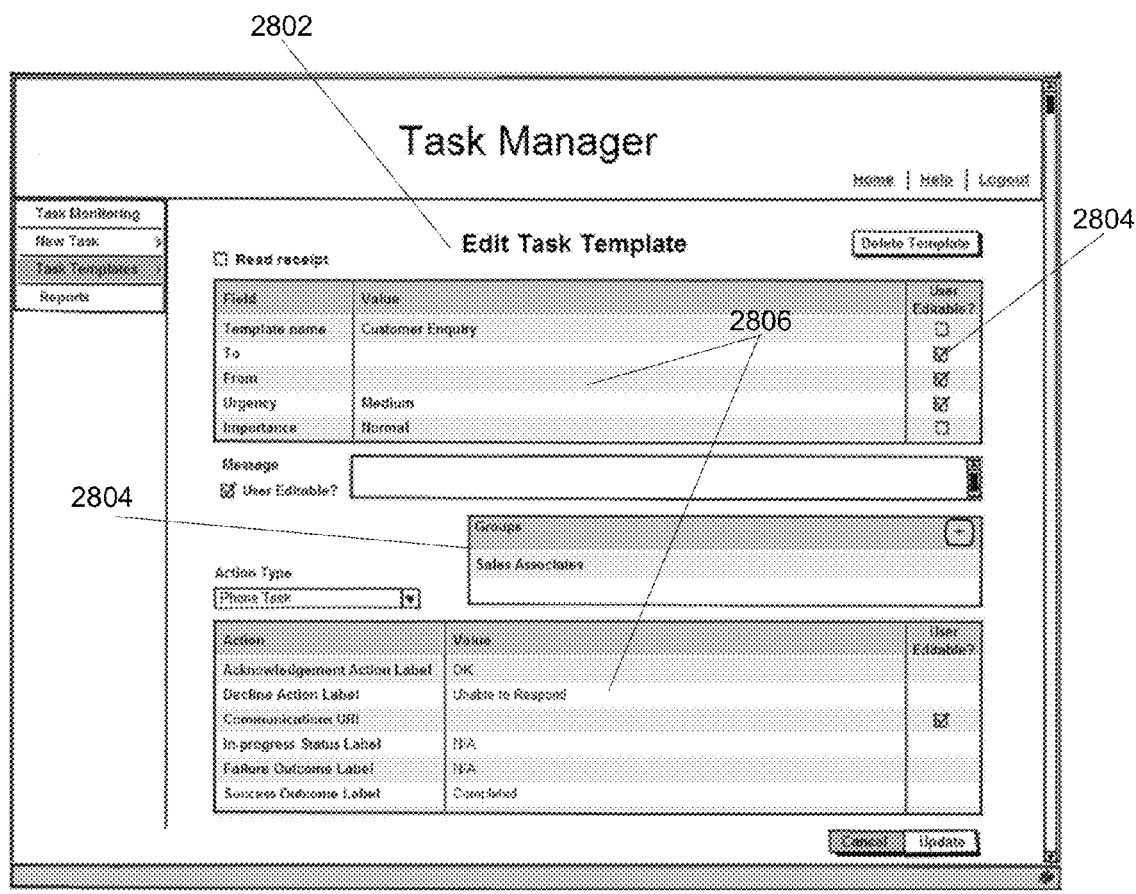

Referring now to FIG. 28, a screenshot 2800 of an exemplary task template editing module 2802 is presented. The task template editing module 2802 permits a system administrator at the administrative computing device 214 to create the preconfigured workflow requests 408 illustrated in FIG. 4 and described in the accompanying detailed description. The system administrator can determine which fields are user editable fields 2804 and preconfigure the default semantics, text, and icons that are to be displayed with the workflow request 301 and tasks. The system administrator can publish the preconfigured workflow requests 408 to specific groups. The task management system 200 can update the preconfigured workflow requests 408 available to each contact based on whether they are a member of the specific groups.

The system administrator can use the preconfigured workflow requests 408 to control the amount of input the users have in creating workflow requests 301. For example, the system administrator can create highly structured workflow requests 408 that facilitate entry of information by the users. An example is a preconfigured workflow request 408 for cleaning a room in a hospital setting. The preconfigured workflow requests 408 can have a workflow name 502 of clean patient room, and have a default importance 508 of normal. The system administrator can require an information element such as the room number and the cleaning type, along with selectable entries that include the list of room numbers at the hospital or section of the hospital, and cleaning types such as standard clean, disinfection, disinfections with fluorescent marking test, and so forth. These lists of entries can be used to both limit entry of information by the users and also to facilitate easy quick selection of commonly used selections. The preconfigured workflow request 408 can include optional information elements such as a message 510 box that allows the user to enter comments about the task.

The message 510 box can use embedded data elements that can be populated using contextual information to facilitate user selections, such as the room number, type of clean, etc. For example, a field in the message 510 can be: [room number]. This makes it possible for the user to double tap the field to select it and overwrite with the real data, for example the list of rooms associated with the field [room number]. More structured message creation process are also possible where the message is selected from a list of options and then any parameters are collected enabling the message field to be auto assembled The system administrator can set the available responses for acknowledgments or responses, such as acknowledged, accept, defer acceptance, accept with action, and cannot comply among other suitable responses. The defer acceptance selection permits the users to asynchronously negotiate a response time for accepting or rejecting the workflow request 301. For example, the first user would receive a message that the second user has received and reviewed the workflow request 301 but not responded with an accept or reject selection. The system administrator can configure the preconfigured workflow requests 408 so that the second user can respond with their own response 303. Once a user has accepted the workflow request 301, the user can be presented with two new response options, for example "task started" and "cannot complete". After the user has started the task, the user can be presented with two completion options, "task completed" and "cannot complete". The text options can be configured by the system administrator to tailor the task management system 200 to their organization's requirements.

The responses can include implicit actions, such as an accept response to a workflow request 301 to join a conference call can place the user into the conference call and mark the user's status as busy for the duration of the call. When the user exits the conference call, the workflow request 301 can be completed and a completion status message 311 can be sent to the workflow server 210 and the first user that sent the workflow request 301.

The system administrator can also provide general, unstructured preconfigured workflow requests 408. Unstructured messages can include free form text and digits of fixed or dynamic length, with similar structured elements to the structured preconfigured workflow requests. The system administrator can embed unstructured messages as a component of a task associated with the workflow request, for example to facilitate coordination of communication sessions 302, 308 and permit the users to open the communication sessions 302, 308. The system administrator can also configure what kind of information is logged for the preconfigured workflow requests 408, for example logging exact copies of text messages communicated between the users, logging voice call times and the parties involved in the communication session 302, 308, and so forth.

Preconfigured workflow requests 408 can be distributed to users based on groups, permitting the system administrator to, for example, allow supervisors to use both structured and unstructured preconfigured workflow requests 408, while allowing regular users to use only the structured preconfigured workflow requests 408. The group feature allows an organization's tasks to be filtered so that users only see tasks of interest rather than having a long list of tasks and having to search for relevant ones.

Figure 29:
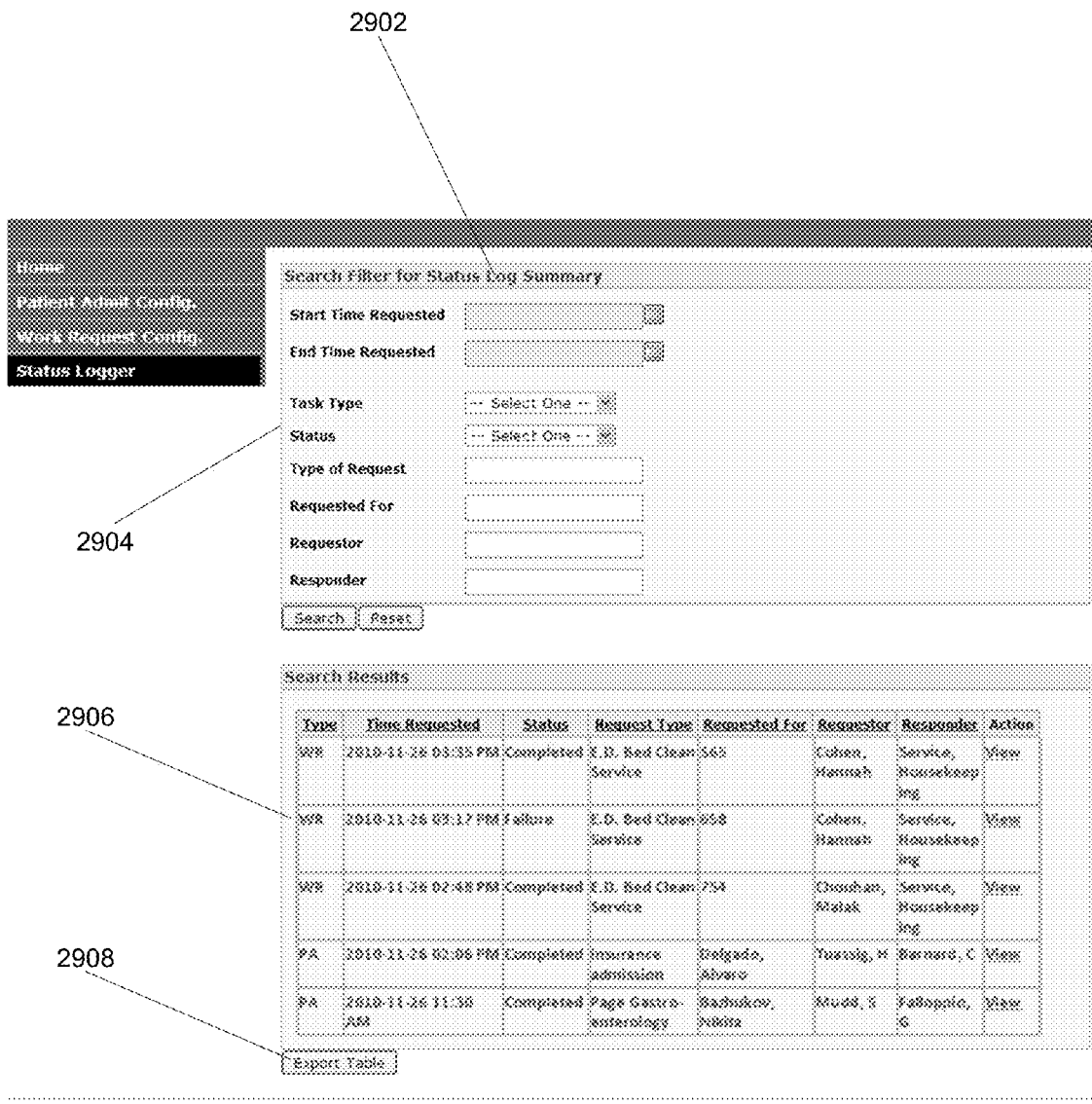

Referring now to FIG. 29, a screenshot 2900 of a workflow analysis module 2902 is presented. The workflow analysis module 2902 permits a system administrator at the administrative computing device 214 to review current workflows being performed, and workflows that have been completed, as well as the status of workflow requests 301. The system administrator can perform actions such as escalation of workflow requests 301, reassignment of workflow requests 301, and so forth.

By logging and reporting information about tasks, workflows, and communications, the system administrator can be presented with detailed information about the various tasks being performed by users and use that information to improve processes and efficiency. The logs can include summary information about each of the alerts, events, communication sessions between parties, voice calls, text messages, workflow requests 301, acknowledgements, tasks, delegated tasks, and escalated tasks, among other information. The logs can include information captured from communication sessions, such as the text content of text messages. The log can be an XML-based log. An example log is presented in Table 1.

TABLE 1

```
<?xml version="1.0" encoding="UTF-8"?>
-<TaskHistory>
    -<TaskEntry>
        <TaskId>2651</TaskId>
        <Title>msgSubject</Title>
        <TaskType>MultiChoice_01</TaskType>
        <TaskTemplatedId>25672570883F8CE92042E17D34E94728F4632FAE</TaskTemplatedId>
        <CompletionStatus>NOT_SET</CompletionStatus>
        <TaskOverdue>FALSE</TaskOverdue>
        <RequesterId>Connexall</RequesterId>
        <ResponderId>samira</ResponderId>
        <DueBy>2012-02-02 04:58:16</DueBy>
        <Importance>0</Importance>
        <Message>testNotif</Message>
        <CallDestination>sip://1234567</CallDestination>
        <StartTime>2012-02-01 23:57:16.718</StartTime>
        <TerminatedOn>2012-02-01 20:02:50.524</TerminatedOn>
    </TaskEntry>
    -<TaskEntry>
        <TaskId>2744</TaskId>
        <Title>msgSubject</Title>
        <TaskType>PhoneTask_01</TaskType>
        <TaskTemplatedId>25672570883F8CE92042E17D34E94728F4632FAE</TaskTemplatedId> <CompletionStatus>COMPLETED_FAILURE</CompletionStatus>
        <TaskOverdue>TRUE</TaskOverdue>
        <RequesterId>Connexall</RequesterId>
        <ResponderId>samira</ResponderId>
        <DueBy>2012-02-02 06:29:15</DueBy>
        <Importance>0</Importance>
        <Message>testNotif</Message>
        <CallDestination>sip://1234567</CallDestination>
        <StartTime>2012-02-02 01:28:15.687</StartTime>
        <EndTime>2012-02-02 09:50:14.342</EndTime>
        <TerminatedOn>2012-02-02 09:50:14.342</TerminatedOn>
        -<ActionLogs>
            -<ActionLog>
                <timestamp>2012-02-02 01:28:24.281</timestamp>
                <message>READ</message>
                <originator>P</originator>
            </ActionLog>
        </ActionLogs>
    </TaskEntry>
</TaskHistory>
```

The system administrator can search and sort log information using the search filter 2904 function. A display of search results 2906 can display the log information. The results can be exported using the export selection 2908, for example to a comma delimited file. The system administrator can perform analysis of selected tasks and workflows. The system administrator can evaluate information from logs captured by the workflow server 210 and the mobile computing devices 206, 208. Each of the mobile computing device 206, 208 and the workflow server 210, or any other suitable element of the task management system 200 can capture a log of events as they occur. Events can include, among other things, each workflow request, acceptance, rejection, deferred acceptance, inquiry, text message, notification, alert, escalation, and delegation of a task, collectively messages, and can include time stamps. The events can also include information regarding the status of performance, such as the commencement of performance, or the completion of a task, collectively the performance of the task. Information regarding the performance of the task can be based on information received from the second user, or can be information received from an external device, such as a sensor or another computing system, and can include a time stamp. Generally, as each event occurs, a time stamp associated with each of the events can be captured. The task management system 200 can log all events associated with each task, workflows, and communications with time stamps for later review.

Figure 30:
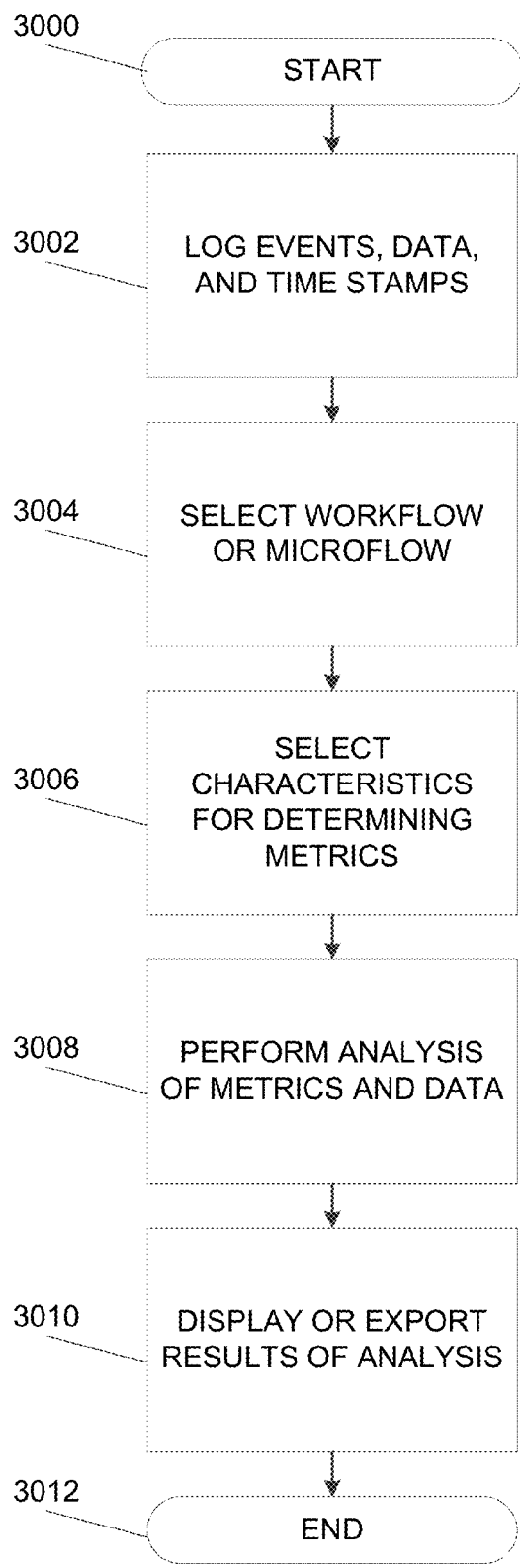
FIG. 30 is a flow diagram of an operation of the task management system.

Referring now to FIG. 30, a method of analyzing workflows is presented. Processing starts at start block 3000. Processing continues to process block 3002. At process block 3002, logs of events, data such as message contents, and timestamps are collected. Processing continues to process block 3004. At process block 3004, the system administrator selects the workflow or microflow to be analyzed. The system administrator can select for example, an individual task associated with a microflow, all events of a microflow, or ranges of workflows. For example, the system administrator can select events based on the type of task, a user, a period of time, or a combination of parameters. Processing continues to process block 3006. In process block 3004, the system administrator can further choose a characteristic to be measured. For example, the characteristic can be tasks that have not been completed, among other characteristics. Processing continues to processing block 3008.

In process block 3008, the system administrator can perform analysis of the selected data, for example by computing metrics of the characteristics, comparing those metrics with other metrics, and comparing metrics to data. Analytic tools can be applied to analyze the information and develop metrics about the performance of tasks, aspects of communications and collaboration, and individual's performances. The analysis and metrics can be used to analyze business processes and create improvements. For example, the comparison can be compared a metric related to tasks that have not been completed for a particular type of task, with the same metric for all types of tasks to see if the selected task is, on average, less frequently completed than other types of tasks. The analysis can include both real-time analysis (e.g., for creating alerts or performing workload management) and post-processing aspects (e.g., for evaluations or compliance).

Processing continues to process block 3010. In process block 3010, the results can be displayed on a display screen to the system administrator, or exported to a file or report. Processing then ends at end block 3012. Visualization tools can be applied to display the information, logs, and metrics. For example, the results can be displayed as text information, or graphical presentations such as charts, histograms, and other graphical presentations can be used. Views of the logs, metrics, and analyzed data can be sorted by task, by type of workflow request 301, by user, and by metric among other views. The system administrator can use views of the logs to highlight and identify areas of issues, for example tasks that are past due, users with too many tasks or outstanding workflow requests, users who have accepted workflow requests 301 and then abandoned the tasks, types of tasks that are typically performed later than requested, users that are not completing tasks on time, and so forth. The system administrator can view the logs in real time or substantially real time.

The system administrator can process the log information to ensure compliance with personnel, corporate, or regulatory objectives. For example, personnel compliance can include workload management and performance evaluations. Corporate compliance can include business efficiency evaluations or compliance with internal procedures. At a system level, the system administrator can process the log information to see the amount of collaboration between and within departments and analyze the degree of organizational communication. The system administrator can check to see if confidentiality screens are being complied with or if inter disciplinary consultations on large projects are being performed as intended. Regulatory compliance can include evaluation performance of workflows to ensure that federal, state, and local regulations are being met. The logs can be used as evidence during certification or for insurance purposes.

The system administrator can also analyze the patterns of communication between parties to determine social networking patterns, for example to analyze interdepartmental and intradepartmental collaboration and individual roles within groups. For example, the system administrator can develop metrics that show the type of communications used and the frequency of communications to determine whether the types of messages in preconfigured workflow requests are sufficient or whether users typically need to fall back to person-to-person voice calls. The system administrator can also develop metrics that show supervisor-to-subordinate communications, for example to show that proper channels are being used for delegating tasks. The system administrator can also develop metrics based on peer-to-peer communications, and communications within groups, for example to show communication patterns typical for certain tasks or users.

The system administrator can analyze the patterns of communications at the level of the microflow, between workflows, or within an aggregation of workflows. This can be used to develop metrics for analyzing an individual's participation level and status, leadership ability, or recognized subject matter expertise or skill level. The system administrator can create a view of a users' work-related social networks by analyzing users' statically defined user group memberships, dynamic roles, and associated group memberships combined with their history of communications, favorites (e.g., other users), and task/message interactions. The analysis can include the type, frequency, and characteristics of the interactions to develop metrics concerning how often a user communicates with other users, which users commonly interact with one another, correlations of individuals to their group membership, and so forth. The analysis can be an aggregated social network view, a view based on workflow type or task type, a view based on an individual, or another suitable kind of view. The system administrator can analyze the metrics over a period of time, for example to perform trend analysis to view how metrics or data are changing over time. The metrics and data can be combined or correlated with other business data.

Example analyses and metrics include, but are not limited to, analysis and metrics relating to subject matter expertise, task distribution, task completion rates, staffing issues, and usefulness of preconfigured tasks. With regards to subject matter expertise, the analysis can enable the system administrator to determine which users are contacted the most often by other users during the performance of tasks or in general. For example, the analysis can provide information about which users have skill expertise recognized by other users, and which users are the kinds of users that are relied on for information versus which users are identified as dependable performers of tasks. The analysis of both kinds of users can provide the administrator with information for determining the proper combination of users to meet their organization's staffing requirements. The analysis can also identify those users that perform key mentorship roles within an organization, have strong leadership skills, or frequently provide assistance to other users. With regards to task distribution and staffing issues, the metrics and data can determine the distribution of tasks completed by users in a particular time period, and provide information about the mean, median, high, low, or other statistically useful variable. This can help the system administrator understand individual strengths or weaknesses, or identify particularly good teams. The system administrator can use the metrics and data to identify potential staffing issues or other inefficiencies that cause performance to fall outside target criteria or thresholds. With regards to task completion rates, the metrics and data can identify tasks that are not completed on time, and allow the system administrator to review communication details to understand potential causes and reasons for unsuccessful completions. The system administrator can also identify tasks that are abandoned or uncompleted to determine the root causation. For example the system administrator can correlate activities with individuals, busy times, shift changes, types of tasks, and so forth to discover problems. The system administrator can use this information to change procedures to improve completion rates.

The system administrator can review and analyze microflows to determine the usefulness of preconfigured workflow requests 408, predetermined phrases 1702, and predetermined completion phrases 2702 among other aspects of the task management system. For example, the system administrator can review communication sessions and messages to determine those tasks where users resort to fallback communications outside of those provided by the preconfigured workflow requests 408, predetermined phrases 1702, and predetermined completion phrases 2702. This can provide the system administrator with information about how to make modifications to increase efficiency, for example by adding new predetermined phrases 1702. This allows the system administrator to customize the context-specific aspects of the task management system 200 to increase user efficiency and provide a more useful interface to the users of the task management system 200.

The above descriptions of various components and methods are intended to illustrate specific examples and describe certain ways of implementing a task management system 200 as disclosed and described here. These descriptions are neither intended to be nor should be taken as an exhaustive list of the possible ways in which these systems and modules can be made and used. A number of modifications, including substitutions of systems and modules between or among examples and variations among combinations can be made. Those modifications and variations should be apparent to those of ordinary skill in this area after having read this document.

What is claimed is:

1. A computer-implemented method for handling a microflow, said microflow comprising at least one communication session, said method comprising:
   receiving, at a processor, a workflow request from at least one of a plurality of heterogeneous applications, wherein said workflow request includes a task associated with the microflow, and
   at least one contact address associated with the task;
   associated with receiving the workflow request, enabling a processor to
      open at least one collaboration communication session with one of the at least one contact address and at least one other contact address, said collaboration communication session being embedded within the microflow, and
      send at least one response to the workflow request addressed to at least one of the at least one contact address and at least one other contact address;
   storing the task in a workflow queue in a memory;
   dynamically prioritizing, at the processor, the task; and
   associated with execution of the microflow, enabling a processor to
      open collaboration communication session with one of the at least one contact address and at least one other address, said collaboration session being embedded within one of the at least one communication sessions,
      sending, from the processor, a status associated with performance of the task, and
      sending, from the processor, a completion status of the task.

2. The method of claim 1, wherein the response is selected from at least one of
   an acceptance of the workflow request,
   an inquiry regarding the workflow request,
   a rejection of the workflow request, and
   a request to defer an acceptance of the workflow request.

3. The method of claim 1, wherein at least one of the collaboration communication sessions is transmitted in accordance with a medium selected from the group consisting of
   a text message,
   a multimedia message,
   an email message,
   a voice call,
   a video call,
   a conference call,
   a web-based session using a uniform resource locator, and
   a call to an interactive voice response system.

4. The method of claim 1, wherein the operation associated with execution of the microflow further includes:
   presenting, at a human machine interface, the task,
   wherein presenting the task includes at least one of:
      displaying an icon associated with the type of task,
      displaying a shape associated with a priority of the task,
      displaying a color coding associated with the priority of the task,
      displaying a shading associated with the priority of the task,
      displaying an alert,
      presenting an audible message about the task,
      presenting an audible alert, and
      presenting a vibratory alert.

5. The method of claim 4, wherein the operation associated with execution of the microflow further includes:
   receiving, at a human machine interface, a selection of the task; and sending, from the processor, at least one of
  a call request, and
  a message to the contact address associated with the task.

6. The method of claim 1, wherein the workflow request further includes at least one of
  a requested priority,
  a requested start time,
  a requested completion time,
  a requested length of time to complete the task, and
  a location for performance of the task.

7. The method of claim 6, wherein the process of dynamically prioritizing the task comprises integrating a prioritization of the task from the heterogeneous source of the workflow request, based at least in part on at least one of
  the difference between a current time and at least one of the requested start time,
  the requested completion time, and the requested length of time to complete the task, and
  a priority based at least in part on at least one of
    the requested priority,
    a priority set by a user override, and
    a priority set in accordance to at least one of
      a business policy rule associated with the task, and
      a regulatory compliance rule associated with the task.

8. The method of claim 1, further comprising:
  presenting, at a human machine interface, the workflow request; and
  receiving, at the human machine interface, an input for responding to the workflow request, and
  wherein the response to the workflow request is based at least in part upon the input.

9. The method of claim 1, further comprising:
  receiving a message that includes at least one of
    a rescind notification of the workflow request,
    a reprioritization of the task, and
    a notification to remove the task from the workflow queue.

10. A non-transitory computer-readable storage medium having computer-executable instructions stored thereon to instruct a processor to perform a method comprising:
  sending, to a first recipient, a workflow request from at least one of a plurality heterogeneous applications, wherein said workflow request is associated with a microflow, said microflow comprising at least one communication session, that includes
    a task associated with the microflow, and
    at least one contact address for addressing, via a collaboration session, a
    message related to the task;
  receiving, via the at least one communication session, a response to the workflow request;
  receiving, via the at least one communication session, a status associated with performance of the task; and logging, in a memory, at least one of
    the workflow request,
    a timestamp associated with sending the workflow request,
    the response to the workflow request,
    a timestamp associated with receiving the response, the status associated with performance of the task, and
    a timestamp associated with receiving the status.

11. The non-transitory computer-readable storage medium of claim 10, further comprising computer-executable instructions stored thereon to instruct a processor to perform the operations comprising:
  escalating the workflow request at the expiration of an escalation timer and prior to receiving a least one of
    a response to the workflow request, and
    a status associated with performance of the task; and
  sending the workflow request to a second recipient.

12. The non-transitory computer-readable storage medium of claim 11, wherein the second recipient is selected from the group consisting of
  an originator of the workflow request,
  an alternate recipient of the workflow request, a
  peer group associated with the first recipient,
  a peer group associated with the second recipient, and
  an administrator.

13. The non-transitory computer-readable storage medium of claim 10, wherein the workflow request further includes at least one parameter selected from the group consisting of
  an address of a first recipient,
  an identification of the type of task,
  an address associated with the contact address,
  a preferred medium associated with the contact address, a requested priority,
  a requested start time,
  a requested completion time,
  a requested length of time to complete the task, and a location for performance of the task, and
  and wherein the processor includes computer-executable instructions stored thereon to instruct the processor to change the parameter in accordance to at least one of
  a business policy rule associated with the task, and
  a regulatory compliance rule associated with the task.

14. A system for handling a microflow, said microflow comprising at least one communication session, said system comprising:
  a computing device having a processor configured to
    receive a workflow request from at least one of a plurality of heterogeneous applications, wherein said workflow request that is associated with the microflow that includes a task, and
      at least one contact address associated with the task,
    perform an operation associated with receiving the workflow request that includes at least one of
      opening a collaboration session with the one of the at least one contact address and at least one other address, said collaboration session being embedded within one of the at least one communication sessions, and
      sending a response to the workflow request that is addressed to at least one of the at least one contact address and at least one other address,
    store the task in a workflow queue,
    dynamically prioritize the task, and
    perform an operation associated with execution of the microflow that includes at least one of
      opening a collaboration session with one of the at least one contact address and at least one other address, said collaboration session being embedded within one of the at least one communication sessions,
      sending a status associated with performance of the task, and sending a completion status of the task;
  a memory configured to store a workflow queue; and
  a communications interface configured to handle at least one of the communication session, and
  a message.

15. The system of claim 14, wherein the computing device is a mobile computing device, and wherein the communications interface is a wireless communications interface.

16. The system of claim 14, wherein the response is selected from at least one of
- an acceptance of the workflow request,
- an inquiry regarding the workflow request, a rejection of the workflow request, and
- a request to defer an acceptance of the workflow request.

17. The system of claim 14, further comprising:
a human-machine interface including at least one of
- a display configured to present at least one of
  - the workflow request,
  - the task,
  - the contact address,
  - a display of an icon associated with the type of task,
  - a display of a shape associated with a priority of the task,
  - a display of a color associated with the priority of the task,
  - a display of a shading associated with the priority of the task, and a display of an alert,
- an audible element configured to present at least one of
  - an audible message about the task, and
  - an audible alert,
- a vibratory element configured to present a vibratory alert, and
- an input means for accepting an input.

18. The system of claim 17, wherein the processor is further configured to
- present, using the human-machine interface, the workflow request; and
- receive, from the human-machine interface, an input, and wherein the response to the workflow request is based at least in part upon the input.

19. The system of claim 14, wherein the workflow request further includes at least one of a requested priority,
- a requested start time,
- a requested completion time,
- a requested length of time to complete the task, and
- a location for performance of the task, and
wherein the processor is further configured to prioritize the task based at least in part on
- the requested start time,
- the requested completion time,
- the requested length of time to complete the task, and
- a priority based at least in part on at least one of
  - the requested priority,
  - a priority set by a user override, and
  - a priority set in accordance to at least one of
    - a business policy rule associated with the task, and
    - a regulatory compliance rule associated with the task.

20. The system of claim 14, wherein the message is selected from the group
- consisting of the response,
- the status,
- the completion status, and
- an inquiry associated with the task, and
wherein a medium for the message is selected from the group consisting of
- a text message,
- a multimedia message,
- an email message,
- a voice call,
- a video call,
- a conference call,
- a web-based session using a uniform resource locator, and
- a call to an interactive voice response system.

* * * * *